US009629756B2

(12) United States Patent
Zilm

(10) Patent No.: US 9,629,756 B2
(45) Date of Patent: *Apr. 25, 2017

(54) FEMALE INCONTINENCE SYSTEM

(71) Applicant: Zilm-RhoMax Products, LLC, Fort Collins, CO (US)

(72) Inventor: William M. Zilm, Glenwood Springs, CO (US)

(73) Assignee: Zilm-RhoMax Products, LLC, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,430

(22) Filed: Dec. 18, 2015

(65) Prior Publication Data

US 2016/0106600 A1    Apr. 21, 2016

Related U.S. Application Data

(63) Continuation of application No. 14/078,143, filed on Nov. 12, 2013, now Pat. No. 9,314,382, and a (Continued)

(51) Int. Cl.
*A61F 13/15* (2006.01)
*A61F 2/00* (2006.01)
(Continued)

(52) U.S. Cl.
CPC ............ *A61F 13/47* (2013.01); *A61F 2/0009* (2013.01); *A61F 13/4702* (2013.01);
(Continued)

(58) Field of Classification Search
CPC .. A61F 13/15; A61F 13/20; A61F 2/00; A61F 12/00; A61F 22/00
See application file for complete search history.

(56) References Cited

U.S. PATENT DOCUMENTS

| 4,678,464 A | 7/1987 | Holtman |
| 5,591,148 A | 1/1997 | McFall et al. |

(Continued)

FOREIGN PATENT DOCUMENTS

| DE | EP0963217 | | 2/1998 |
| DE | EP 0963217 | * | 6/1998 |
| EP | 0963747 | | 6/1998 |

OTHER PUBLICATIONS

Aben Abri-San Air Plus Premium Incontinence Pads at HealthyKin.com, printed Jun. 13, 2013.
(Continued)

*Primary Examiner* — Tatyana Zalukaeva
*Assistant Examiner* — Ilya Treyger
(74) *Attorney, Agent, or Firm* — Santangelo Law Offices, P.C.

(57) ABSTRACT

Particular embodiments of the inventive technology may provide an incontinence pad that includes projection, such as a raised ridge, or a short length projection, that extends from a pad base of and effects application of a force against the urethra of a user (the force, typically upward, that may result from sitting by the user and/or tight fitting shorts and/or pulling a cord attached to the projection); the projection may act to transfer a force from the projection to the urethra. This force may partially or entirely obstruct flow of urine through, or out of the urethra, that might occur otherwise (i.e., without the projection). Another example of the many independent aspects of the inventive technology relates to the provision, as part of an incontinence pad, of a cord that is attached to part of the pad, such as (in only certain embodiments) the aforementioned upward projection.

5 Claims, 22 Drawing Sheets

Related U.S. Application Data continuation of application No. PCT/US2014/065075, filed on Nov. 11, 2014.

(51) Int. Cl.

| | | |
|---|---|---|
| *A61F 13/47* | (2006.01) | |
| *A61F 13/472* | (2006.01) | |
| *A61H 39/04* | (2006.01) | |
| A61F 13/20 | (2006.01) | |
| A61F 13/84 | (2006.01) | |

(52) U.S. Cl.
CPC .. *A61F 13/47218* (2013.01); *A61F 13/47263* (2013.01); *A61H 39/04* (2013.01); *A61F 2013/15146* (2013.01); *A61F 2013/8476* (2013.01); *A61F 2250/0018* (2013.01); *A61F 2250/0059* (2013.01); *A61H 2201/165* (2013.01); *A61H 2205/087* (2013.01)

(56) References Cited

U.S. PATENT DOCUMENTS

| | | |
|---|---|---|
| 6,152,904 A | 11/2000 | Matthews et al. |
| 6,503,238 B1 | 1/2003 | Torstensson et al. |
| 8,147,472 B2 | 4/2012 | Venturino et al. |
| 8,172,819 B2 | 5/2012 | Ashton et al. |
| 8,277,426 B2 | 10/2012 | Wilcox et al. |
| 8,283,515 B2 | 10/2012 | Lagerstedt-Eidrup et al. |
| 8,348,915 B2 | 1/2013 | Vasic et al. |
| 8,357,133 B2 | 1/2013 | Vasic et al. |
| 8,365,737 B2 * | 2/2013 | Mitsui ...................... A61F 5/24 128/830 |

OTHER PUBLICATIONS

U.S. Appl. No. 14/078,413, filed Nov. 12, 2013, entitled "Novel Incontinence Pad".

PCT Application No. PCT/US14/65075, filed Nov. 11, 2014, entitled "Pressure Enhanced Incontinence Pad and Methods".

Poise Impressa website dated Sep. 2, 2014, 5 pages.

PCT Application No. PCT/US14/65075, filed Nov. 11, 2014, entitled "Pressure Enhanced Incontinence Pad and Methods", Search Report dated Feb. 11, 2015, 4 pages.

PCT Application No. PCT/US14/65075, filed Nov. 11, 2014, entitled "Pressure Enhanced Incontinence Pad and Methods", Written Opinion dated Feb. 11, 2015, 5 pages.

\* cited by examiner

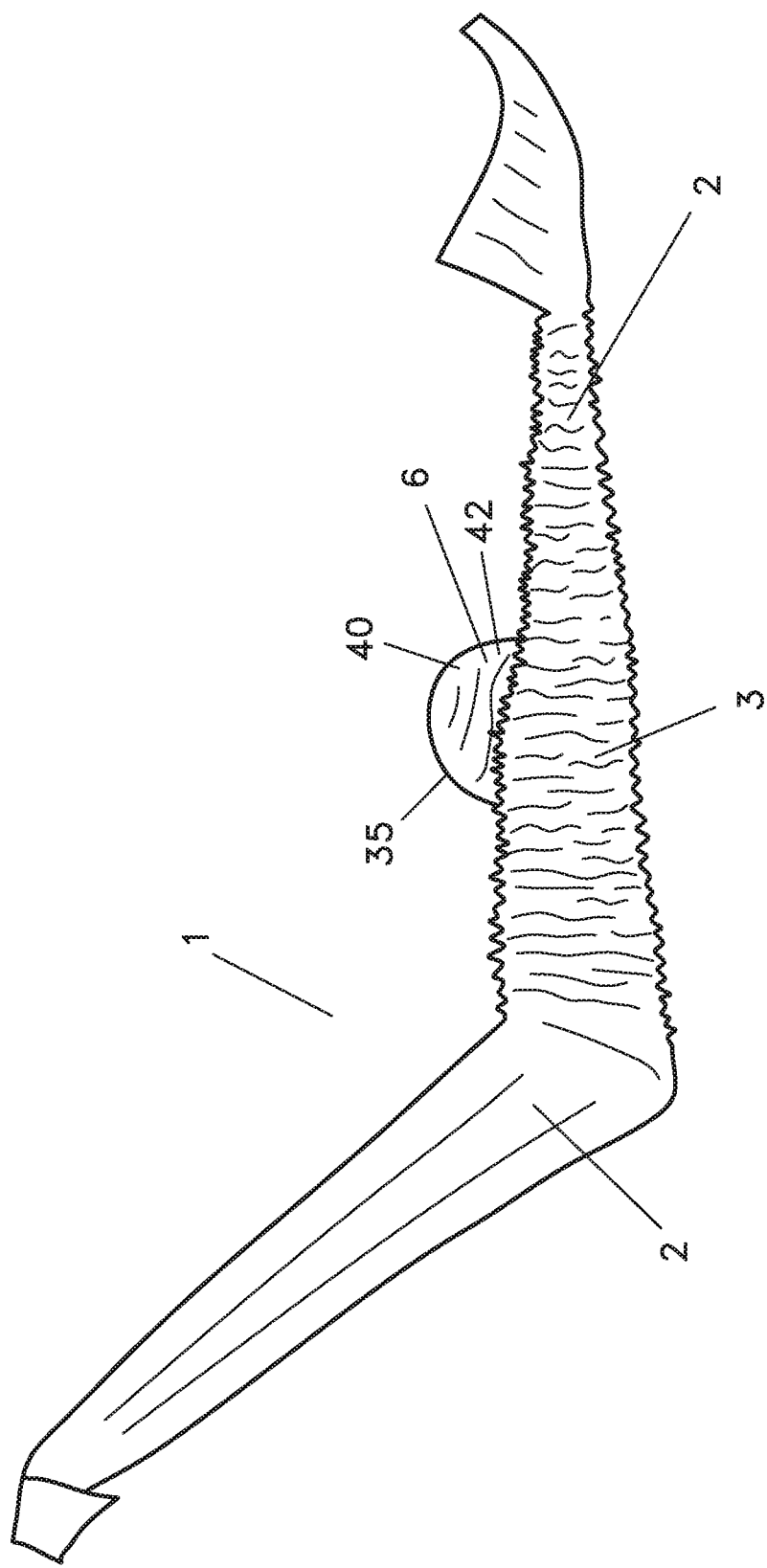

FEMALE INCONTINENCE SYSTEM

This application is a continuation application of U.S. Nonprovisional application Ser. No. 14/078,143, filed Nov. 12, 2013, now U.S. Pat. No. 9,314,382, and PCT patent application No. PCT/US14/65075 filed Nov. 11, 2014, the entirety of which are both hereby incorporated by reference.

TECHNICAL FIELD

The inventive technology disclosed herein has application in the field of mitigating urinary incontinence, and in the related field of mitigating the discomfort and visual impact of urinary incontinence.

BACKGROUND ART

Many men and women suffer from urinary incontinence, to varying degrees, and for various reasons. Whether their particular case is extreme or mild, of long duration or of recent onset, constant or discontinuous, and regardless of the cause, urinary incontinence may pose a significant embarrassing and/or uncomfortable health related challenge. As such, mitigation of urinary incontinence, and of the discomfort and visual impact of urinary incontinence, has long been the goal of many different apparatus and medically related techniques. Indeed, there are numerous different types of incontinence pads (including but not limited to pads, guards, pouches, briefs, and diapers) available for men and women. However, while some conventional pads may indeed effectively capture and retain leaked urine, conventional pads, in focusing only on capture of urinary emissions, do not properly address mitigation of the incontinence itself, i.e., reducing the frequency of emissions and/or reducing the amount of urine leaked during an incontinence event. Even as to those pads that do effectively capture and retain leaked urine, there are still improvements that can be made. Particular shortcomings of conventional pads relative to fluid retention may relate, for example, to fluid spill-out (i.e., leakage of fluid out of the pad along the edges of the pad) and uncomfortable, perhaps noisingly embarrassing fluid slosh (from leaf to right, or vice versa, within the pad), which often may occur while the user is sitting, or moving during sitting. And, perhaps more significantly, as mentioned, conventional pads tend not to provide any mechanism for mitigating the incontinence itself. It is of note that the incontinence mitigation that is achieved via certain embodiments of the inventive technology disclosed herein may have conventionally been achieved only via surgery. As such, particular embodiments of the inventive technology may achieve a desired degree of incontinence mitigation via measures—wearing of an inventive pad—that are much less drastic and interfering than surgery.

SUMMARY OF INVENTION

Particular embodiments of the inventive technology may provide an incontinence pad (whether it contains fluid retention capabilities or not) that features a projection, such as a raised ridge, or a short length projection (or even a short length projection atop a raised ridge), that extends (e.g., upward, when the pad is worn) from a pad base (typically the bottom portion of a pad, when worn) and effects application of a force against the urethra of a user (perhaps upon sitting by the user and/or pulling a cord attached to the projection, thereby transferring an upward force from the projection to the urethra). This force may obstruct the flow of urine through, or out of the urethra. Particular independent aspects of the inventive technology may relate to the provision, as part of an incontinence pad, of a cord that is attached to part of the pad, such as an upward projection (e.g., a raised ridge). Other independent aspects of the inventive technology may include, but are not limited to, a secondary fluid retention element (to enable improved fluid retention), directionally biasing at least a portion of the pad through action of a cord, a targeted pressure element (e.g., a projection, whether it be a raised ridge, a short length projection, a short length projection atop a raised ridge, or other), creating a targeted pressure increase (e.g., via the targeted pressure element), a urethral compressor (e.g., an element of the pad that compresses a urethra, whether of a male or of a female, during wearing of the pad), a nerve trigger element (e.g., a projection) that may trigger a nerve reaction that may result in a mitigation/reduction of incontinence related emissions, a longitudinal absorbency separator (that may split retained fluid into two different fluid retention elements (a right and a left, for example)), a substantially perpendicular structure (e.g., a type of projection that may effect application of a seating-based force to a perineum of a pad wearer), a locationally separate secondary fluid retention element that may provide for ancillary or backup retention of overfill or overflow emissions, a short length projection that may effect force application against a perineum of a user, and an overflow absorbent portion, a comparatively support area absorbent portion and a fluidic communicator between the two.

Objects of the various aspects of the inventive technology are as described below and elsewhere in the application.

It may be an object of at least one embodiment of the raised ridge aspect of the inventive technology to allow for targeted application of force to the urethra, thereby effecting blockage or at least obstruction of flow of urine therethough.

It may be an object of at least one embodiment of the cord aspect of the inventive technology to allow for manual application of force to a pad component (e.g., a raised ridge), thereby effecting an increase in pressure applied by a pad component (e.g., a targeted pressure element such as a projection (e.g., a raised ridge or a short length projection)), thereby effecting blockage or at least flow obstruction through a urethra and mitigating the effects/impact of incontinence.

It may be an object of at least one embodiment of the directional bias aspect of the inventive technology to effect application of force to a pad component thereby effecting blockage or at least flow obstruction through a urethra.

It may be an object of at least one embodiment of the targeted pressure element aspect of the inventive technology to apply pressure to a urethra of a user (e.g., whether by applying pressure to the perineum of a male user or directly to the urethral opening of a female user of the pad), thereby effecting partial obstruction or full blockage of flow therefrom.

It may be an object of at least one embodiment of the urethral compressor (e.g., a projection) aspect of the inventive technology to apply pressure to a urethra of a user. Such pressure may come from, e.g., pulling on a manually graspable cord portion, sitting, or even via a directional bias element.

It may be an object of at least one embodiment of the nerve trigger element aspect of the inventive technology to trigger a nerve that, when triggered, reduces urinary flow (as compared to what flow would be otherwise during an incontinent event), whether by effecting sphincter closure or otherwise.

It may be an object of at least one embodiment of the longitudinal absorbency separator aspect of the inventive technology to separate released emissions into two retention areas—a right side and a left side, thereby mitigating slosh or retained fluid (e.g., during sitting) and/or mitigating leakage of fluid from the pad.

It may be an object of at least one embodiment of the substantially perpendicular structure aspect of the inventive technology to apply pressure to a urethra of a user It may be an object of at least one embodiment of the locationally separate secondary fluid retention element aspect of the inventive technology to provide for an area for overflow from a primary fluid retention element (overflow may occur during sitting, or shortly after an incontinence emission).

It may be an object of at least one embodiment of the separate perineum retention element aspect of the inventive technology to provide for secondary fluid retention in the area of the perineum, thereby providing benefits relative to an increase in the amount of stored fluid, for example.

It may be an object of at least one embodiment of the short length projection aspect of the inventive technology to provide for application of a force to a urethra of a user (particularly at the opening of the urethra of a female user, but also possible at the perineum of a male user).

It may be an object of at least one embodiment of the overflow absorbent portion (with a compressible support area absorbent portion and fluidic communicator portion) aspect of the inventive technology to improve fluid retention and/or prevent or reduce leakage that might otherwise occur.

It may be an object of at least one embodiment of the inventive technology to provide for mitigation of urinary incontinence via non-surgical measures.

Of course, further objects, advantages, and goals of the inventive technology may be as described elsewhere in this application.

BRIEF DESCRIPTION OF FIGURES

FIGS. 8A and 8B show pads with short length projections, while FIG. 8C shows a pad with a raised ridge.

FIG. 15 shows a left side view drawing of an embodiment of an incontinence pad featuring a short length projection.

Figure 1:
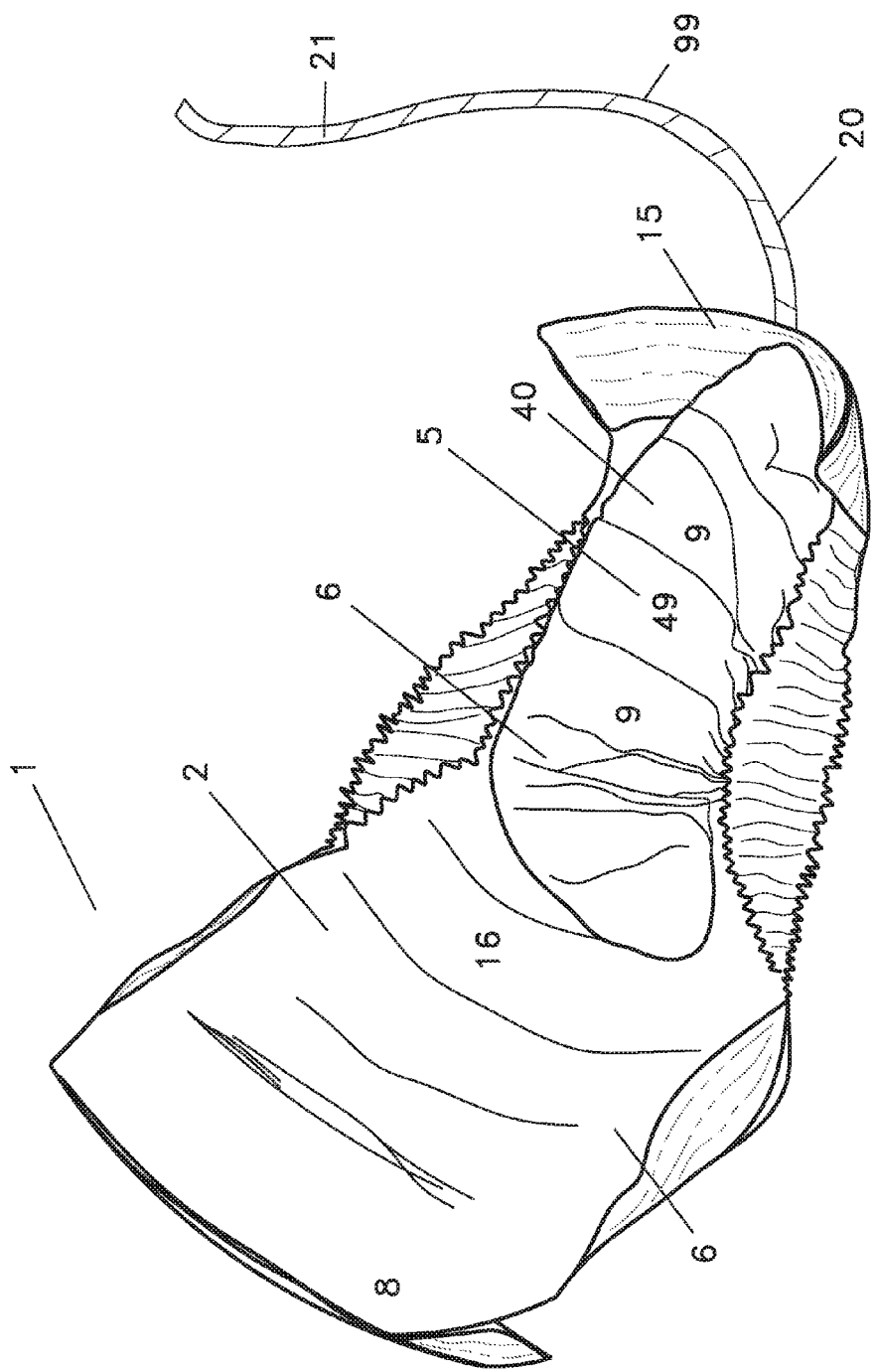
FIG. 1 shows a perspective view drawing of an embodiment of an incontinence pad with a raised ridge from a substantial center of the pad to a substantial posterior end of the pad. One way in which this pad may be formed is via the instructions provided herein that operate on a pad with adhesive on one side.
Figure 2:
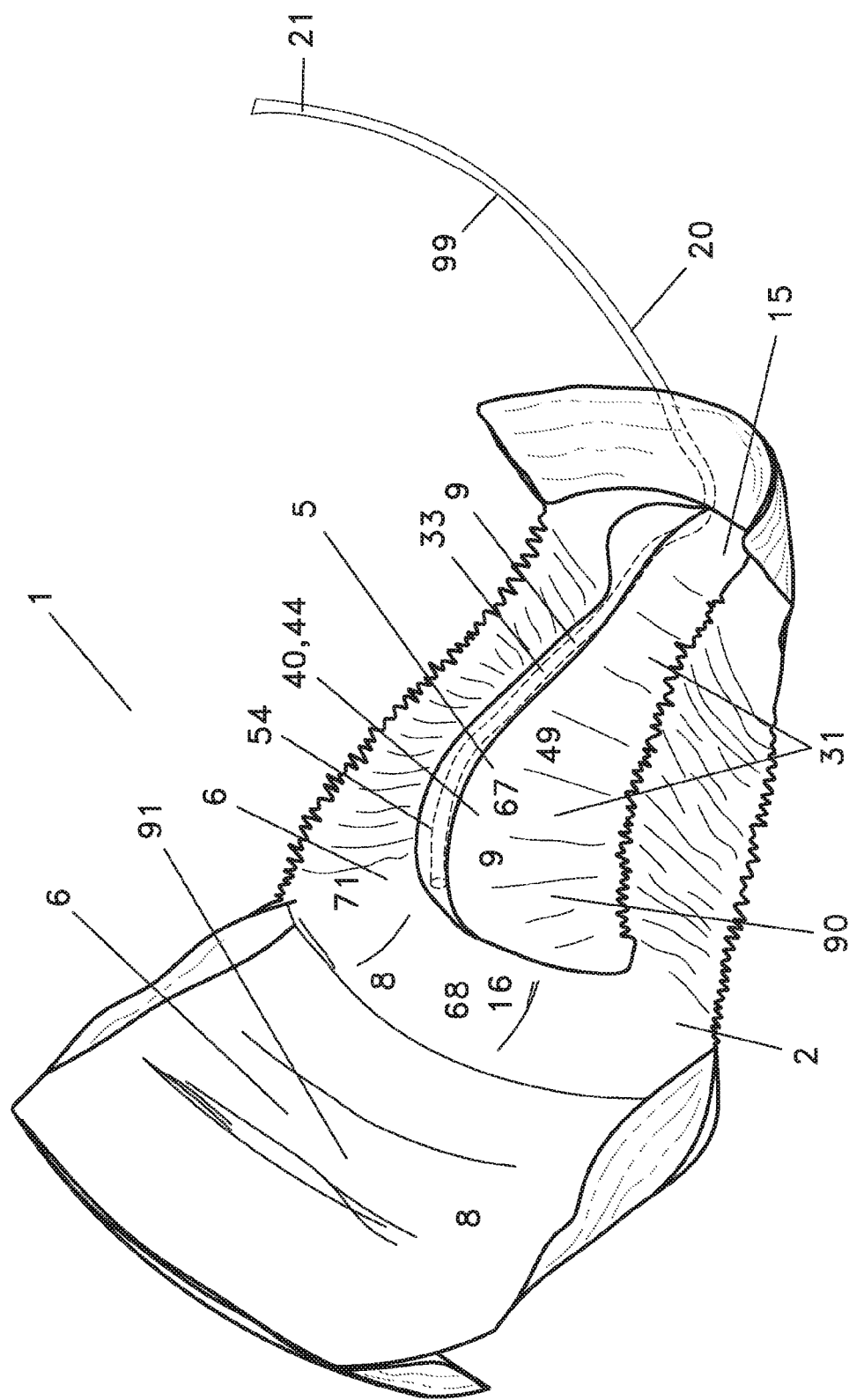
FIG. 2 shows a perspective view drawing of an embodiment of an incontinence pad with a raised ridge from a substantial center of the pad to a substantial posterior end of the pad. The additional cord portion is shown in dashed line (center, mid-height of ridge, although it may also be nearer to or at the top or bottom of the ridge); it is not visible to the naked eye in this particular embodiment.
Figure 3:
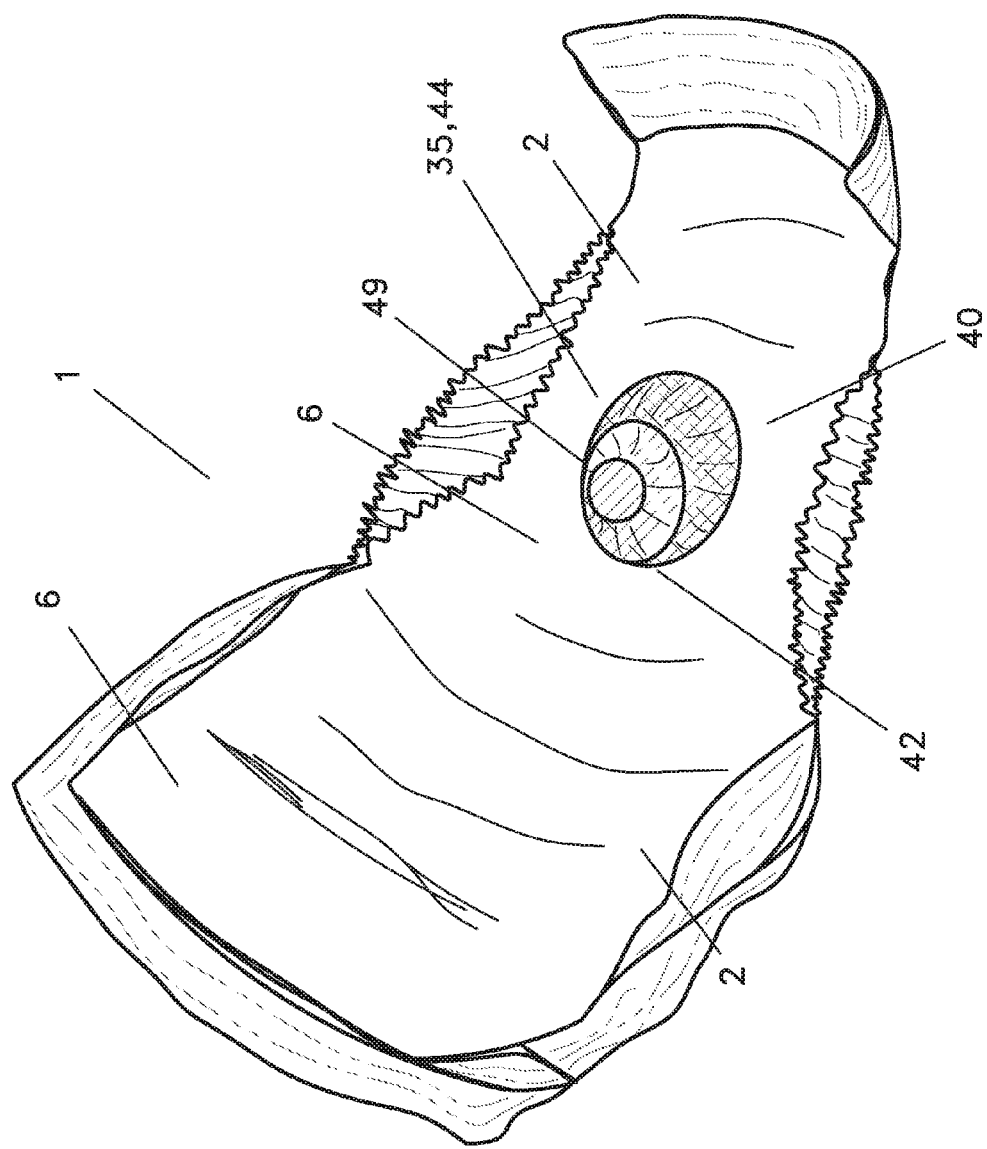
FIG. 3 shows a perspective view drawing of an embodiment of an incontinence pad featuring a short length projection.
Figure 4:
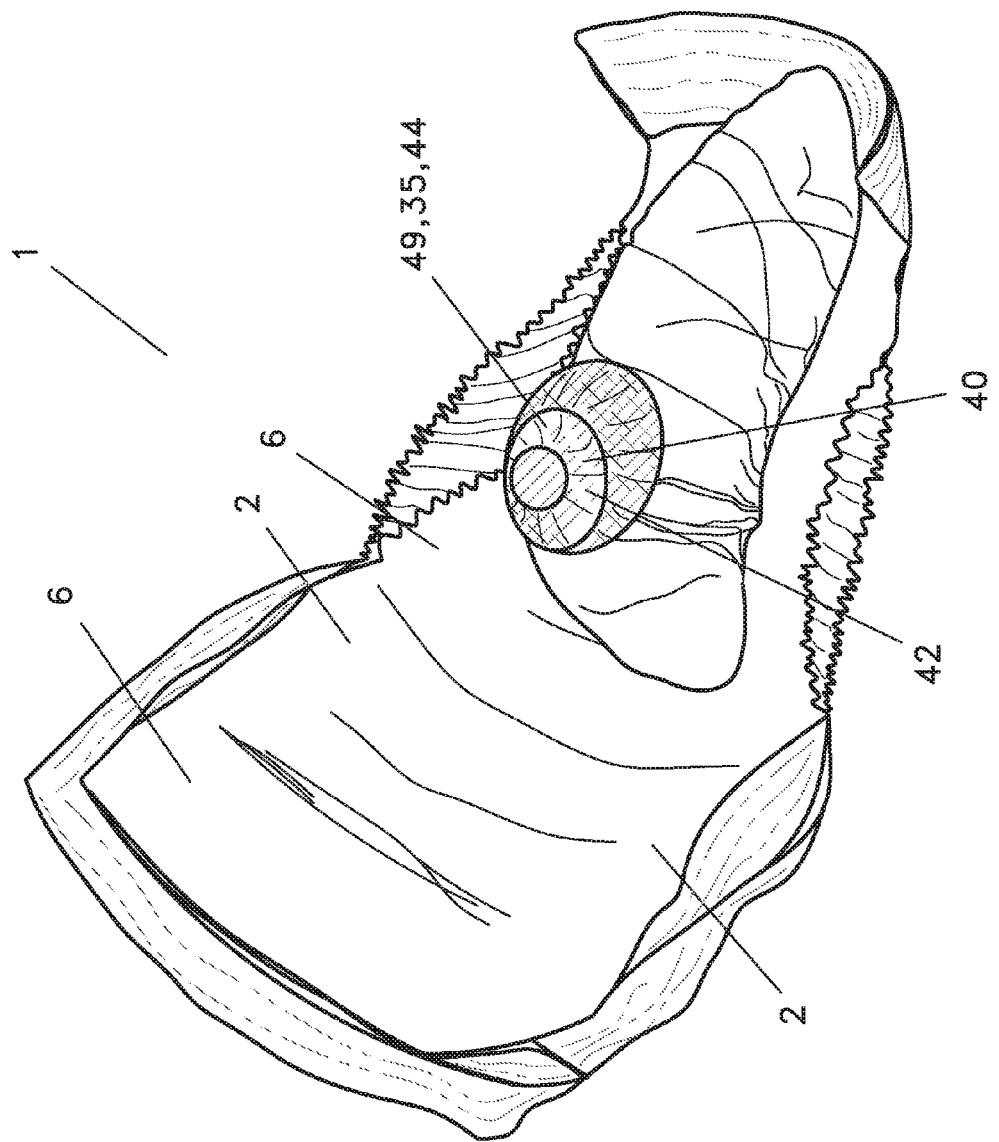
FIG. 4 shows a perspective view drawing of an embodiment of an incontinence pad featuring a short length projection atop a raised ridge (each is a projection alone, and together both form a type of projection).
Figure 5:
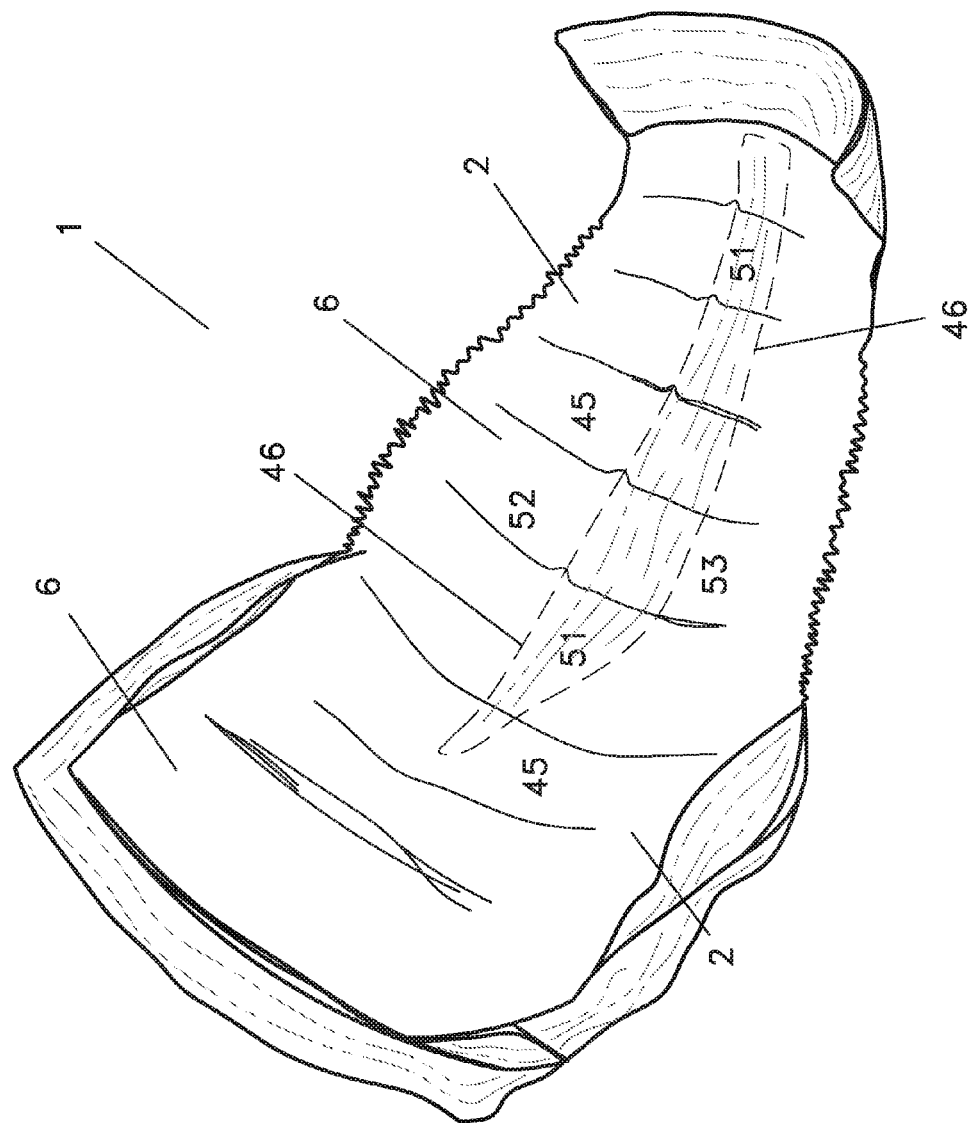
FIG. 5 shows a perspective view drawing of an embodiment of an incontinence pad featuring a substantially longitudinal absorbency separator (shown in dashed line, and perhaps not discernible to the naked eye because it may be entirely within the pad). Such feature may be found in conjunction with any of the independent inventive aspects of the pad disclosed elsewhere herein (e.g., in conjuction with a projection, and/or a cord), or in isolation. The majority of the lower portion of the dashed line is towards the bottom of the pad, while the upper portion is towards the upper layer of the pad. If there were a projection, the separator may, but need not, continue upwards through the bulk of the projection to achieve absorbency separation (into, e.g., right and left halves) within such projection also.
Figure 6:
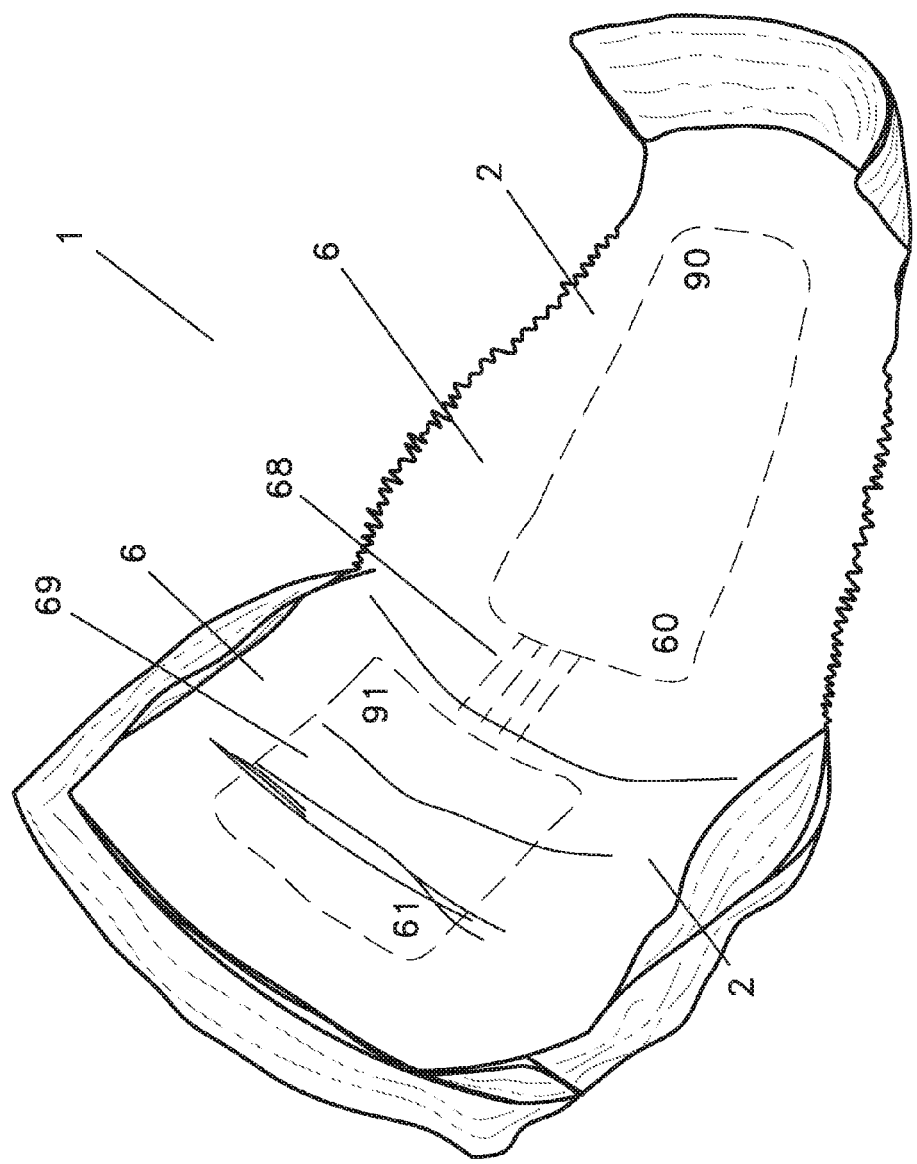
FIG. 6 shows a perspective view drawing of an embodiment of an incontinence pad having a compressible support area absorbent and an overflow absorbent, and a fluidic communicator therebetween (shown in dashed lines, and perhaps not discernible to the naked eye). Such feature may be found in conjunction with any of the independent inventive aspects of the pad disclosed elsewhere herein (e.g., in conjunction with a projection, and/or a cord), or in isolation.
Figure 7:
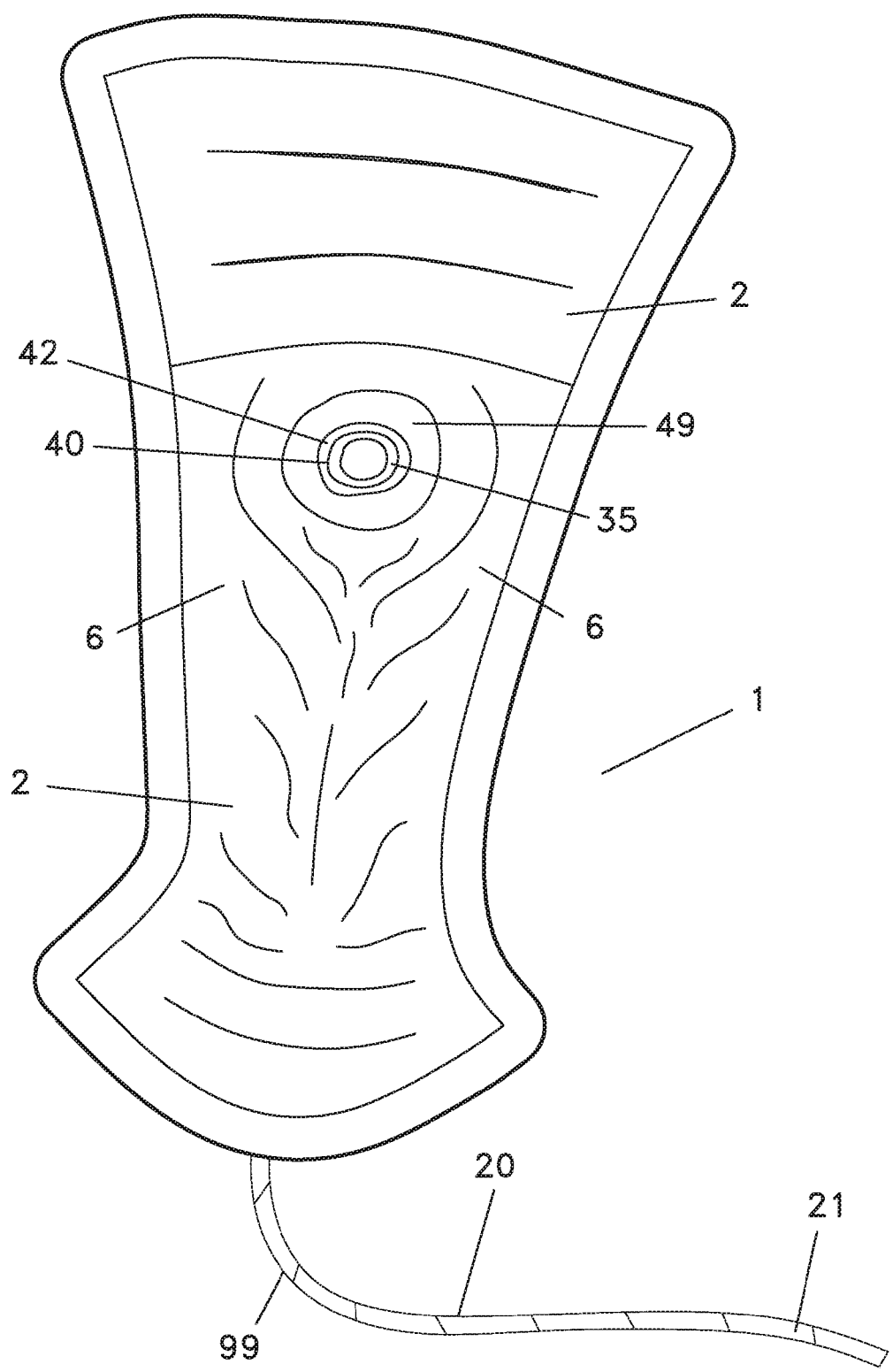
FIG. 7 shows an overhead view (from above) drawing of an embodiment of an incontinence pad having a short length projection and a manually graspable cord.
Figure 8:
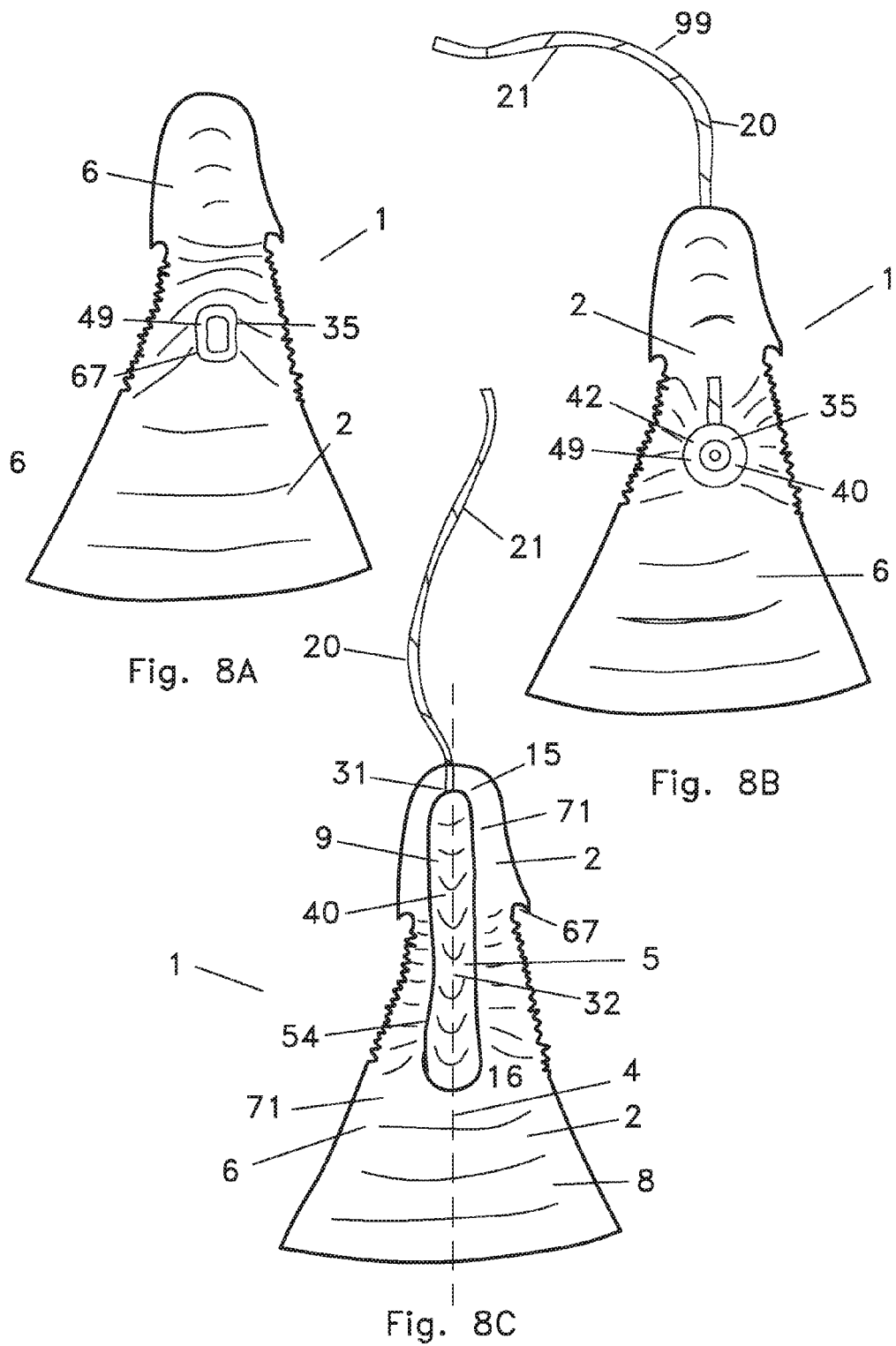
FIGS. 8A, 8B and 8C show overhead view drawings of an embodiment of an incontinence pad.
Figure 9:
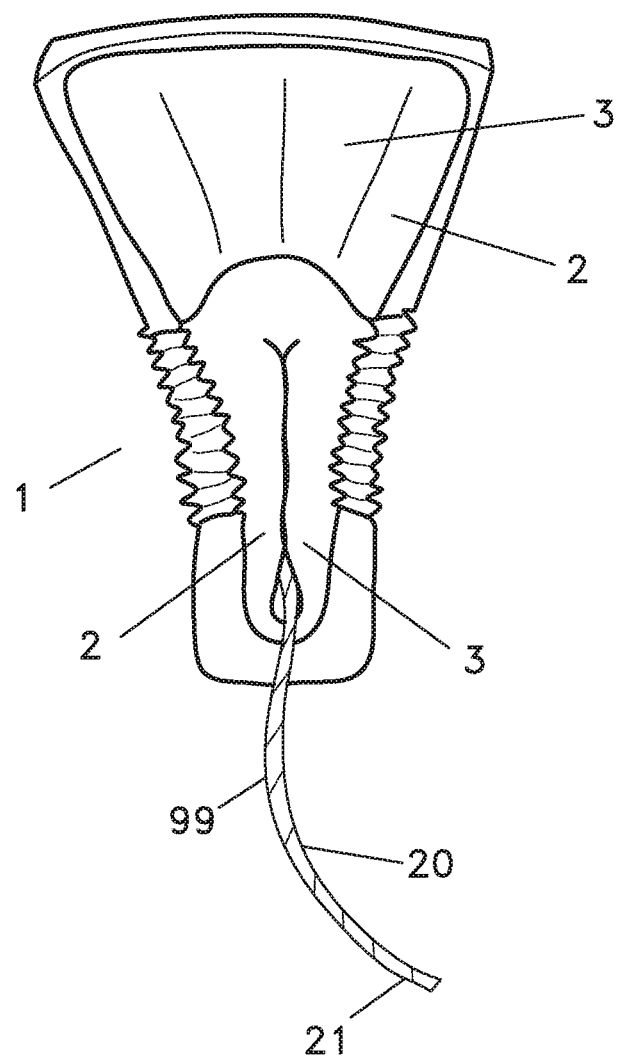
FIG. 9 shows a drawing from below of an embodiment of an incontinence pad.
Figure 10:
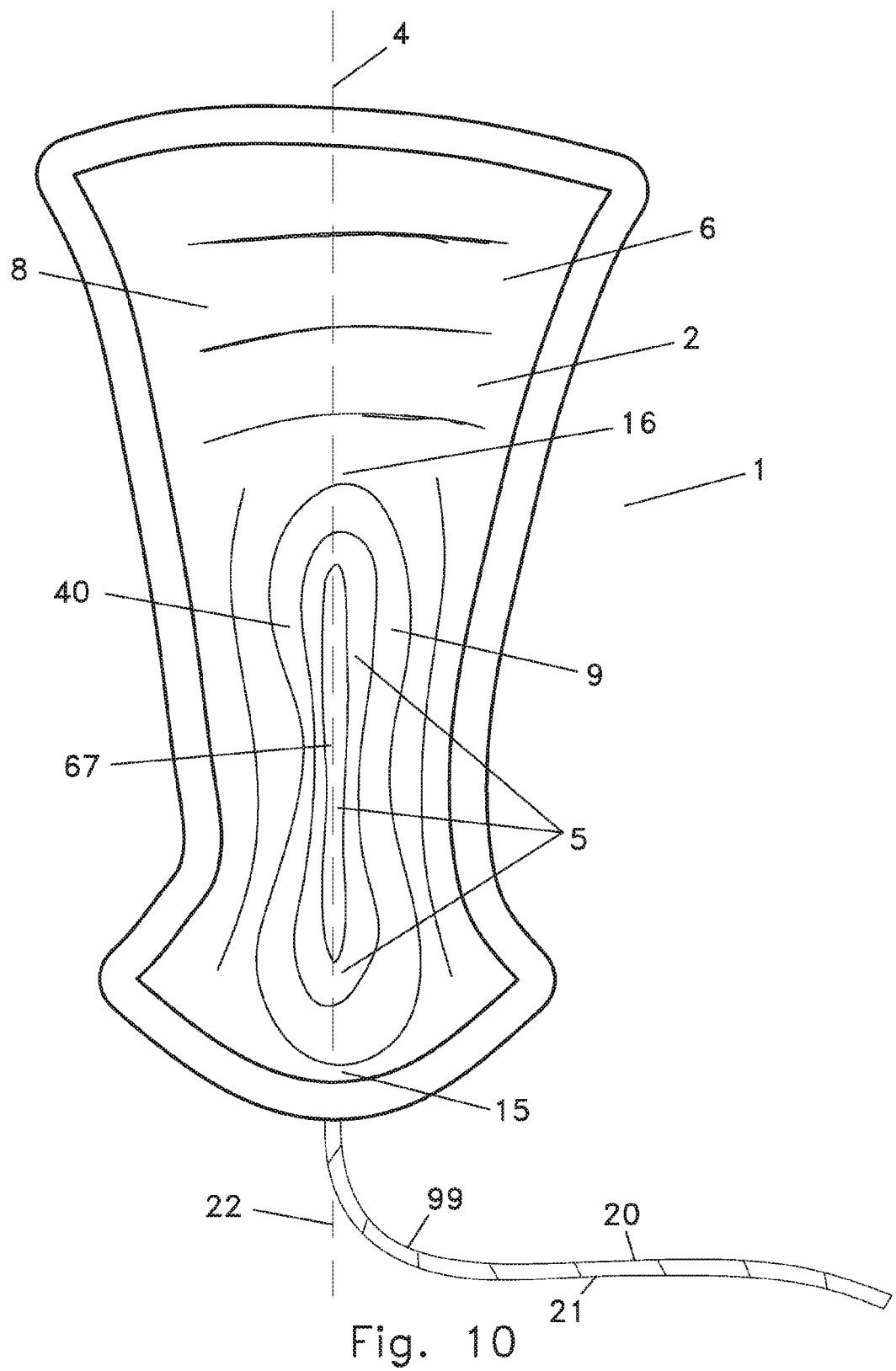
FIG. 10 shows an overhead view drawing of an embodiment of an incontinence pad featuring a raised ridge.
Figure 11A:
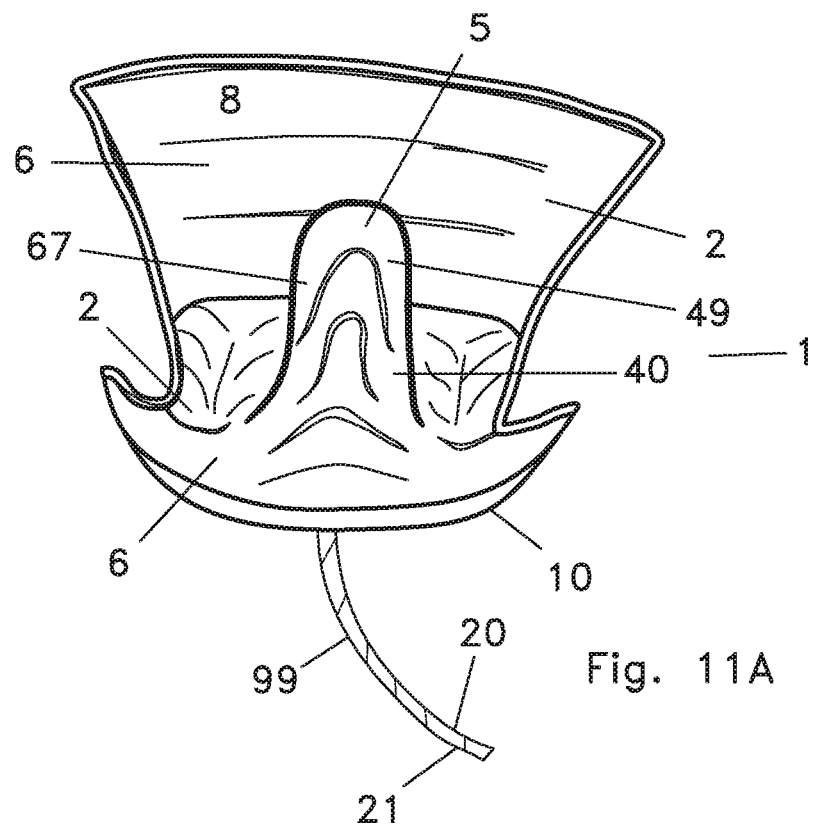
FIG. 11A shows a rear view drawing of an embodiment of an incontinence pad featuring a raised ridge.
Figure 11B:
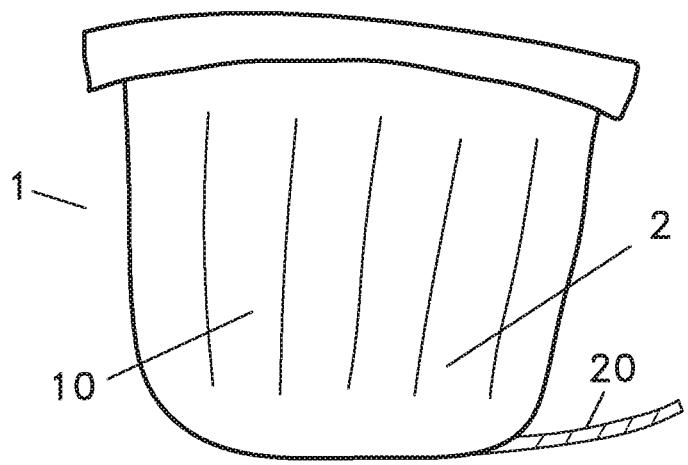
FIG. 11B shows a frontal view (view from the front) drawing of an embodiment of an incontinence pad.
Figure 12A:
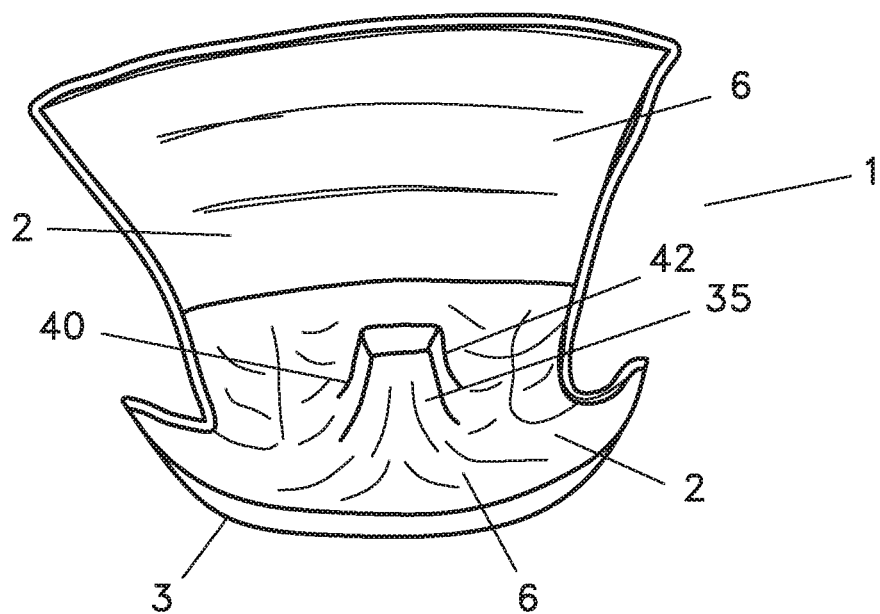
FIG. 12A shows a rear view drawing of an embodiment of an incontinence pad featuring a short length projection.
Figure 12B:
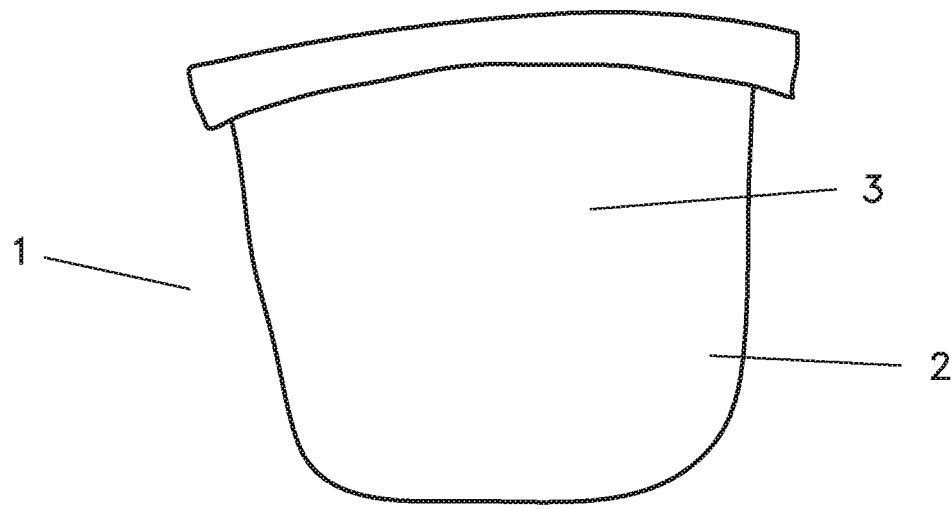
FIG. 12B shows a frontal view drawing of an embodiment of an incontinence pad.
Figure 13:
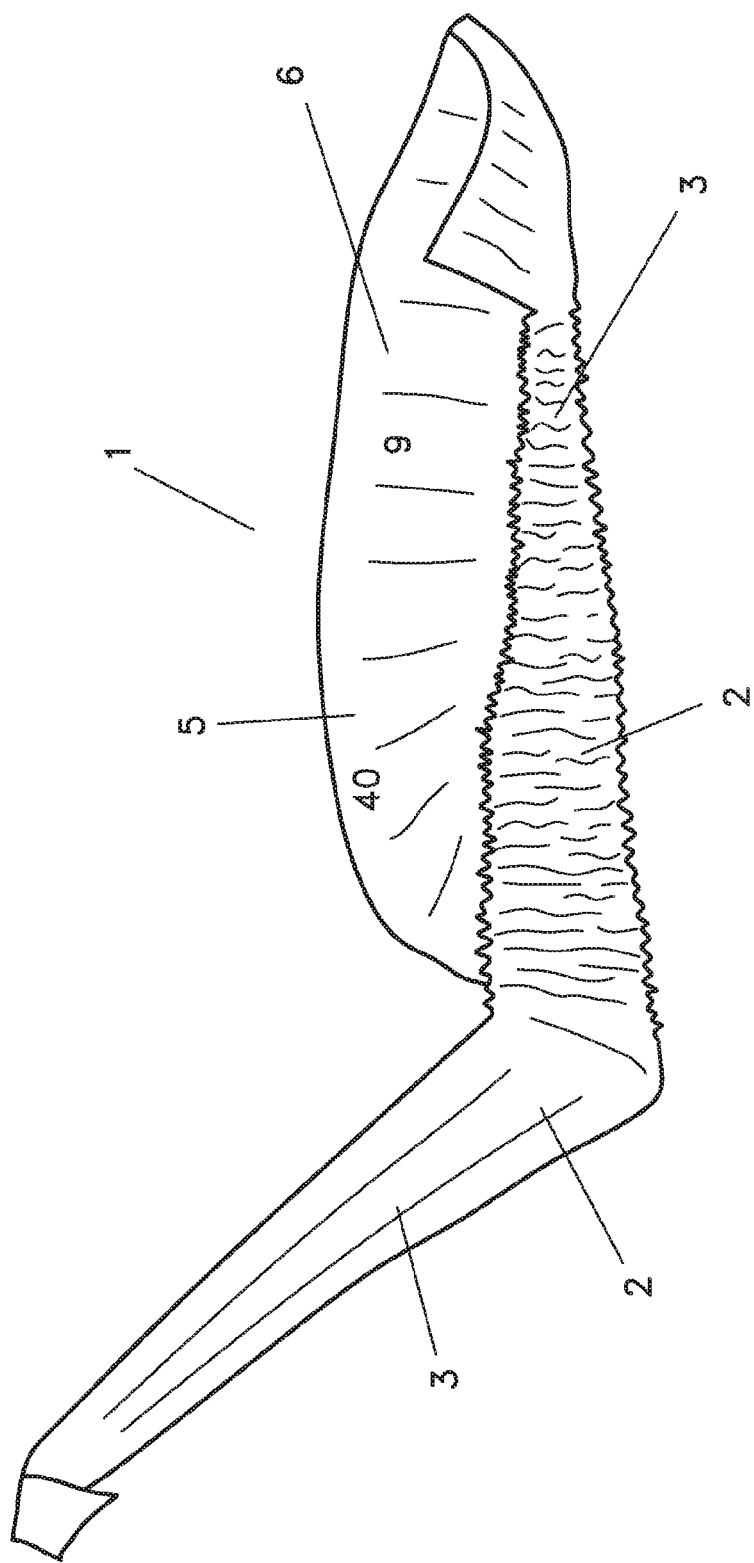
FIG. 13 shows a left side view drawing of an embodiment of an incontinence pad featuring a raised ridge.
Figure 14:
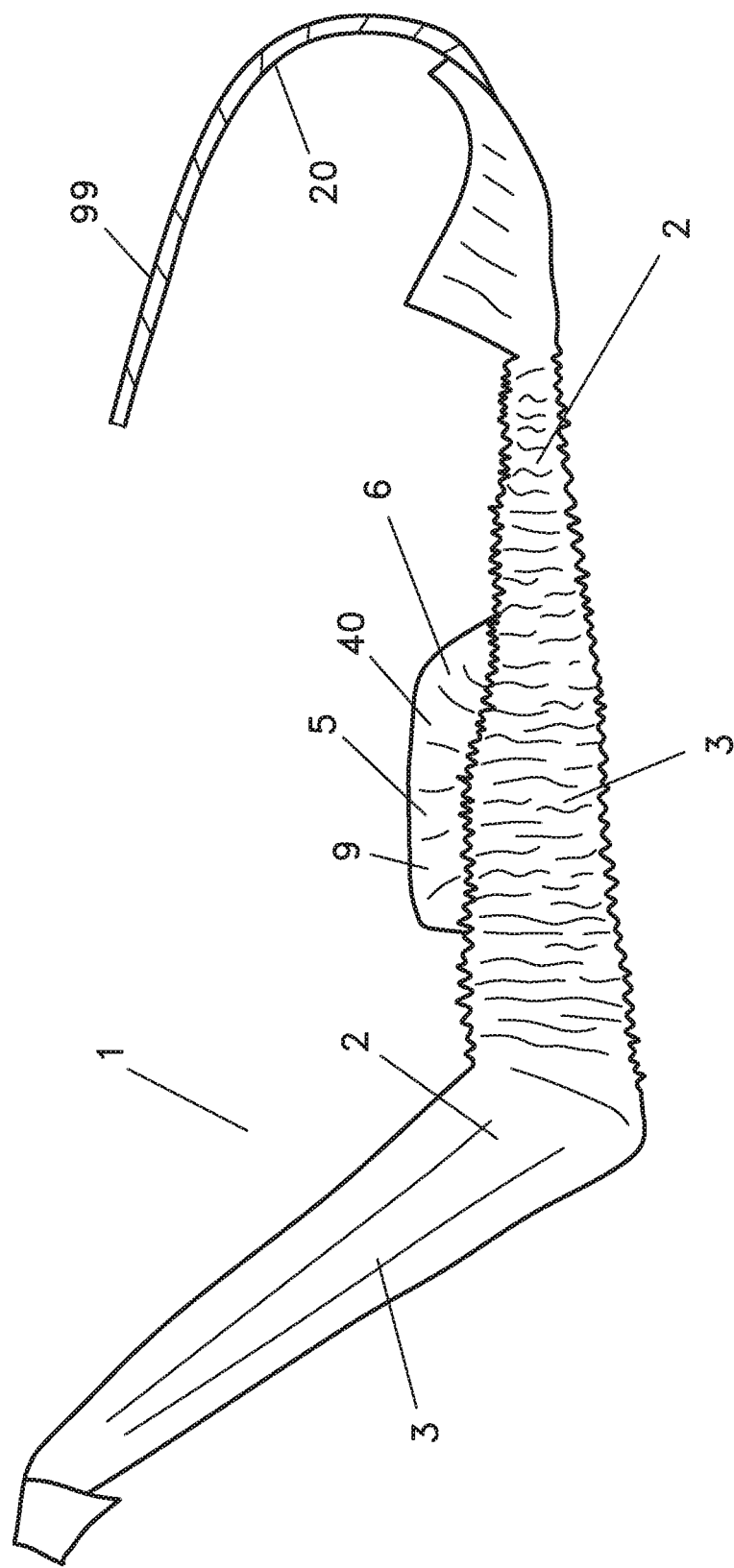
FIG. 14 shows a left side view drawing of an embodiment of an incontinence pad featuring a raised ridge.

Note that each the features shown in the figures are not necessarily required features (for example, elastic cuffs are shown in many of the pads depicted in the drawings and are indeed preferred, but they are not required features in inventive pads). Indeed, it is only the scope of the claims that limit the breadth of the inventive technology. It is also of note that all appearances, in the drawings, of a particular component (where that component is called out or referenced with a number in the written description below) might not be called out in the figures with that number. Further, a particular part as shown in the drawings can serve as an exemplary type of more than one named (and perhaps numbered) component. For example, the raised ridge is a type of projection; it is also a type of nerve trigger element.

MODES FOR CARRYING OUT THE INVENTION

At least one embodiment of the inventive technology may be described as an incontinence pad 1 that comprises a base 2 having an outer (skin distal, or clothing proximal) surface 3 capable of being established (upon being "donned" by a user) against clothing of a user when the incontinence pad is worn by the user, with the base having a centerline 4 (e.g., a longitudinal centerline, that perhaps passes within a mid-sagittal plane of the user/wearer of the pad); a raised ridge 5 established above part of the base on at least a portion of the centerline; and an inner (skin proximal, or clothing distal) surface 6 capable of being established adjacent skin of the user when the incontinence pad is worn by the user. The base, in certain embodiments, may constitute the bulk of the pad. It may, in certain embodiments, at least appear visually as being similar if not identical to conventionally available pads (note that particular inventive aspects, e.g., a projection, a cord, an absorbency separator, a secondary retention element, etc., may be added onto or incorporated within the base). The raised ridge may be raised above (or closer to the skin of the pad user than) the surface of the base that is towards skin of the wearer. The term ridge does not require any particular shape. In preferred embodiments, it may have a length in a mid-sagittal plane of the pad user that is greater than its width (the left to right (with respect to a pad user) distance of the ridge) (see, e.g. FIGS. 1, 2, 8C, 13, 14, 16A, and 17A). In certain embodiments, the ridge may, perhaps (but not necessarily) in coordination with other possible independent inventive aspects (e.g., attached cord), effect pressurization against a urethra of the user (particularly a male user). Such pressurization may effectively mitigate incontinence via physical blockage (perhaps only partially, but ideally completely) of urine flow therethrough. It may pressurize the urethra from a side thereof, perhaps forcing it against bone or tissue (e.g., pubic symphysis, or other part of the pelvis) that obstructs movement of the urethra in the direction of the pressure (and/or perhaps the urethra is akin to a taut string that, because of its tension, is substantially immovable in the direction of the pressure). In this manner, the inner walls of the urethra may be forced towards one another to at least partially obstruct flow. In certain embodiments, urethral flow may be obstructed by application of pressure at the urethral opening.

More particularly as to surfaces of the certain pad embodiments, the inner surface (configured for establishment against skin of a pad user/wearer) may comprise a base inner surface 8 and a raised ridge inner surface 9. The outer surface may be liquid impermeable (so as to prevent passage of liquid to clothing outside of the pad); it may be a liquid impermeable outer layer 10. In certain embodiments, part of the inner surface of the pad may be a liquid impermeable inner surface. Of course, in such embodiments, the entirety of the inner surface is not liquid impermeable (as urine must pass into the pad to be retained thereby). Indeed, for retention of urine emissions, the base may comprise a liquid absorbent material 12 (whether it be entirely liquid absorbent, or include such liquid absorbent material only in a portion or portions thereof). Note that a portion of, or the entirety of the inner surface of the pad may be one way liquid impermeable (liquid can enter from the interior of the space defined by the pad when worn, but cannot pass from the pad towards the interior of the space defined by the pad (i.e., towards the skin of the user).

In particular embodiments, at least part of the base and at least part of the raised ridge are of the same material (e.g., as where the ridge is fabricated as a formed, perhaps molded part of the material of the base). Accordingly, in such embodiments, an inner, skin proximate portion of the base and an inner, skin proximate portion of the raised ridge may be different portions of the same layered, sheet like material. The raised ridge may comprise a comparatively more rigid support component 13 (i.e., compared to the upper portions of the raised ridge) that provides support for it; the comparatively more rigid support component may be established below the same layered, sheet like material. Examples of such comparatively more rigid support component include but are not limited to cardboard, foam, plastic, dried fiber, and reinforced material generally. In embodiments where the base and the raised ridge are discrete pad components, still, in such embodiments, the raised ridge may comprise a comparatively more rigid material that provides support for it. However, in certain embodiments, there might not be a comparatively more rigid support component; indeed, support for the raised ridge may be provided by same material that makes up the bulk of the interior of the raised ridge. This may be as seen in the case where the raised ridge is formed by pinching together adjacent components of the base of the pad (such pinched together portions may be held together via adhesive (perhaps at interposing faces that would be along the longitudinal centerline of the completed pad), or stitching, as but two examples).

More particularly as to shape, size and configuration of the ridge, in certain embodiments, it may have one end that terminates substantially at a longitudinal end (e.g., a posterior end 15, towards the rear of the user) of the pad and another end that terminates at a non-end portion 16 of the pad. Regardless of where the anterior end of the raised ridge is situated, in certain embodiments, with respect to the pad wearer, the posterior end of the raised ridge may terminate in the intergluteal cleft of the wearer when the pad is worn by said user (wearer). In certain embodiments, this may be below, at, or above the anus of a user when the pad is worn by the user. In particular embodiments, a posterior end of the pad terminates higher (above ground that a wearer of the pad is standing on) than does the posterior end of the raised ridge of the pad. Note that the raised ridge typically is longer (front to back) than any short length projection (whose length is specified below). However, a raised ridge is a type of projection (where projection is not specified as short length).

Note that any of the features indicated in this specification may be featured relative to a pad base having a wide variety of shapes (including but not limited to triangular, rectangular, polygonal, perhaps with curved corners, curved, scooped, bucket shaped, and any of those shapes found in conventional pads).

Further, as to shape/size of the raised ridge, the raised ridge may be the to have a cross-sectional shape in a coronal plane (an anatomical plane of the body of the user) when worn by a user. Such shape may be triangular, half-circular disc shaped, block shape and chamfered edge block shape, as but a few examples. It may be small (in width in the coronal plane cross-section) enough to allow for effective pressurization of at least part of the perineum by the raised ridge. In particular embodiments, the raised ridge may have a front end to rear end length that is less than a front end to rear end length of a normal or typical perineum of a user. In others, the raised ridge may have a front end to rear end length that is greater than a front end to rear end length of a typical user's perineum. In others, the length may be substantially the same (i.e., the length of the raised ridge may be within +/−5% of the typical front to rear length of a perineum). In any event, in preferred embodiments of the inventive technology featuring a raised ridge, the raised ridge is positioned on the base portion such that at least part of the raised ridge is established under the perineum during use of the pad by the user. Ways in which pressure may be applied to the perineum by the ridge include but are not limited to: sitting on the pad (by a user/wearer thereof), pressure application of tight-fitting clothing (e.g., briefs) worn around the pad, and tensioning of the raised ridge (perhaps by operation of a cord attached thereto) that effects upward pressure of the raised ridge on the perineum.

As discussed, in particular embodiments, a raised ridge may be configured to apply a flow blocking pressure to the urethra of the user during use of the pad by the user, when the user is in a seated position (or via other mechanisms as explained immediately above). In such embodiments, a height, shape and stiffness of the raised ridge may be sufficient to apply the flow blocking pressure to the urethra of the user during use of the pad by the user, when the user is in a seated position. However, in certain embodiments, even when a user is in a non-seated position, height, shape and stiffness of the raised ridge, and tightness of clothing worn around the pad may be sufficient to apply the flow blocking pressure to the urethra of the user during use of the pad by the user. In certain embodiments, such "non-seated" position flow obstruction may be achieved though action of a cord attached to the raised ridge portion.

A method to mitigate incontinence comprising the steps of: establishing an absorbent pad in a genital area 17 of a user; establishing a raised ridge adjacent a perineum 18 of the user; and absorbing at least a substantial portion of any emissions from the user as a result of the incontinence within the absorbent pad. Note that the first two steps may be accomplished by a user/wearer while donning ("putting on") an incontinence pad that comprises the absorbent pad and the raised ridge 5 (and perhaps other features also, of course). Note that the raised ridge may indeed by absorbent itself. The method may further comprise the step of applying localized pressure to the perineum of the user at least partially through use of the raised ridge of the pad, thereby compressing the urethra of the user with the localized pressure and preventing the involuntary urination. In particular embodiments, the step of applying localized pressure may include applying pressure exerted from under the raised ridge by a sitting surface in response to sitting by the user on the surface; in those (and other) embodiments, the step of applying localized pressure may include applying pressure exerted by briefs that are tight fitting (e.g., "tighty whitey's", instead of boxers). In the case where boxers are worn, a cord attached to the pad, that can be used effect application of pressure from the raised ridge (or other projection) to the urethra of the user, may be particularly useful and effective. In certain embodiments, the step of applying localized pressure may include applying pressure through action of a cord 20 that may be attached to the raised ridge (in any manner, for example, via adhesive where the raised ridge is adhered around it, via stitching, via tying, as but a few examples). Particular embodiments may include the step of securing the pad in position (which may be more than simply "putting on" (donning) the pad); such step may be achieved at least in part by compressing part of the pad in the intergluteal cleft through use of a user's buttocks' bias towards each other (operation of a cord, or simply lifting the back of the pad, indeed self-administering a mild "wedgie," (e.g., may assist in overcoming this bias initially and establishing the pad (perhaps only the raised ridge part of it, or just a portion of such raised ridge) in the intergluteal cleft)). The step of securing the pad in position may comprise the step of manually grasping a manually graspable cord 99 (a cord that has at least a portion 21 that can be manually grasped) attached to the pad and pulling the cord upward and rearward (behind the user). Note that the cord may be attached to at least a portion of the pad that is along a longitudinal centerline of the pad (along at least a portion of the centerline), such as the raised ridge (which may also be established along at least a portion of such centerline). The step of compressing part of the pad may comprise the step of compressing a raised ridge (which may be a portion of a pad that also comprises a base). The cord may be established along substantially the entire length of the raised ridge, or along only a portion of it (which typically, but not necessarily, include the posterior portion of the raised ridge).

Another aspect of the inventive technology, more directly addressing fabrication methods, may be described as a method of fabricating an incontinence item (e.g., an incontinence pad) wherein the incontinence item comprises a base and a raised ridge element 5 that has a centerline 4 (e.g., a longitudinal centerline that is substantially within a mid-sagittal plane of a pad wearer), the method comprising the steps of: fabricating the base, the base having at least a portion that is absorbent and having a centerline 22; and fabricating the raised ridge element 5 to be positioned along at least a portion of the centerline of the base. In certain embodiments, the step of fabricating the raised ridge element may comprise the step of fabricating the raised ridge element to be detachable from the base (e.g., via hook and loop fastener, for example); perhaps the raised ridge element is re-attachable to, and re-positionable on, the base.

In certain embodiments, the fabrication method may further include the step of configuring so the raised ridge element has a centerline that lies substantially within the mid-sagittal plane of a user of the pad. In certain preferred "raised ridge" designs, the pad is configured so that while the user of the pad is in a seated position, the raised ridge applies a pressure to the perineum of the user, the pressure sufficient to obstruct (a term that includes only partially obstruct) involuntary urine flow through the urethra.

Note that in certain designs, the step of fabricating the raised ridge may comprise the step of fabricating the raised ridge so that the raised ridge has at least one end that extends beyond a longitudinal end of the base element. In certain other designs, the step of fabricating the raised ridge may comprise the step of fabricating the raised ridge so that the raised ridge has an end that terminates substantially at a posterior end of the pad. In either case, the step of fabricating the raised ridge may comprise the step of fabricating the raised ridge so that, while the pad is worn by a user, a posterior portion of the raised ridge is established in the intergluteal cleft of the user. Such posterior end of the raised ridge may terminate in the intergluteal cleft, below, at or above the anus of a user, and posteriorly of a scrotum of a male user, when the pad is worn by the user. In such embodiments, the step of fabricating the base may comprise the step of fabricating the base so that the posterior end of the pad terminates higher than does the posterior end of the raised ridge, when the pad is worn by the user.

Figure 18A:
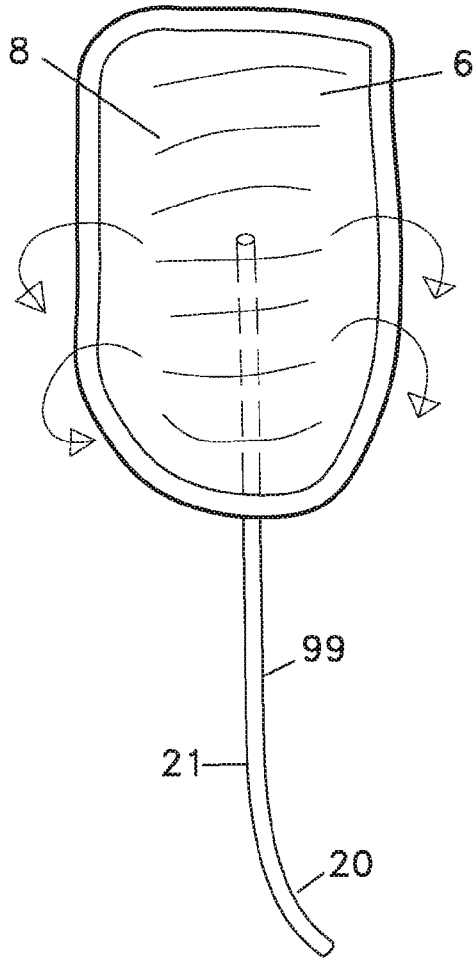
FIG. 18A shows an overhead view drawing of an embodiment of a conventional incontinence pad that can be formed (perhaps even by a purchaser thereof) into a novel inventive pad with a raised ridge (and perhaps a cord) as described herein. The arrows show the direction (downward and rotationally inward (about a longitudinal axis) a portion of the pad may be folded in order to create a raised ridge (perhaps about a cord, as shown).
Figure 18B:
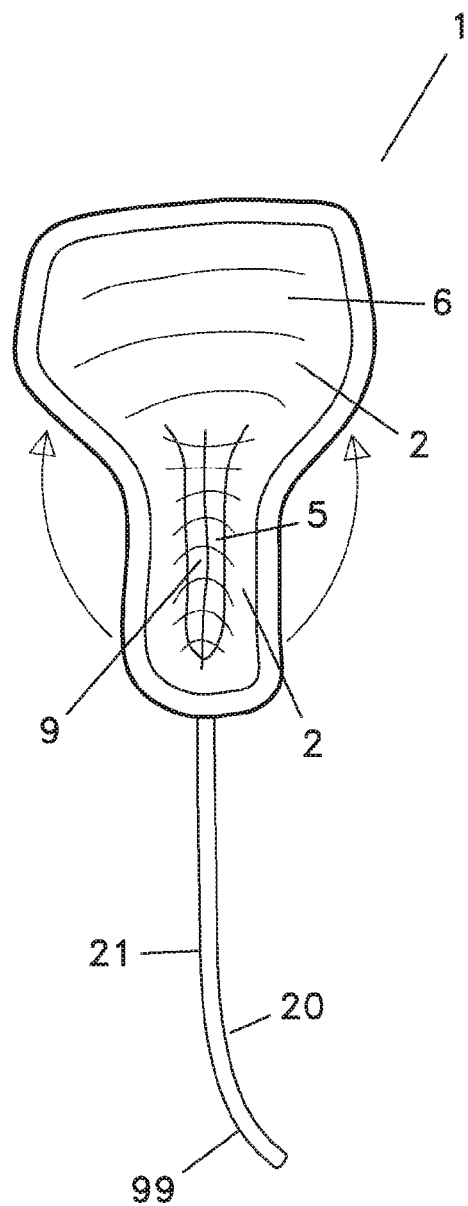
FIG. 18B shows an overhead view drawing of an embodiment of an inventive incontinence pad formed according to FIG. 18A (and related instructions). Arrows show the direction in which parts of the pad may be folded to put the entire pad in a configuration for shipping, storage and/or sale (e.g., the lower half may be folded up into the upper half).
Figure 19:
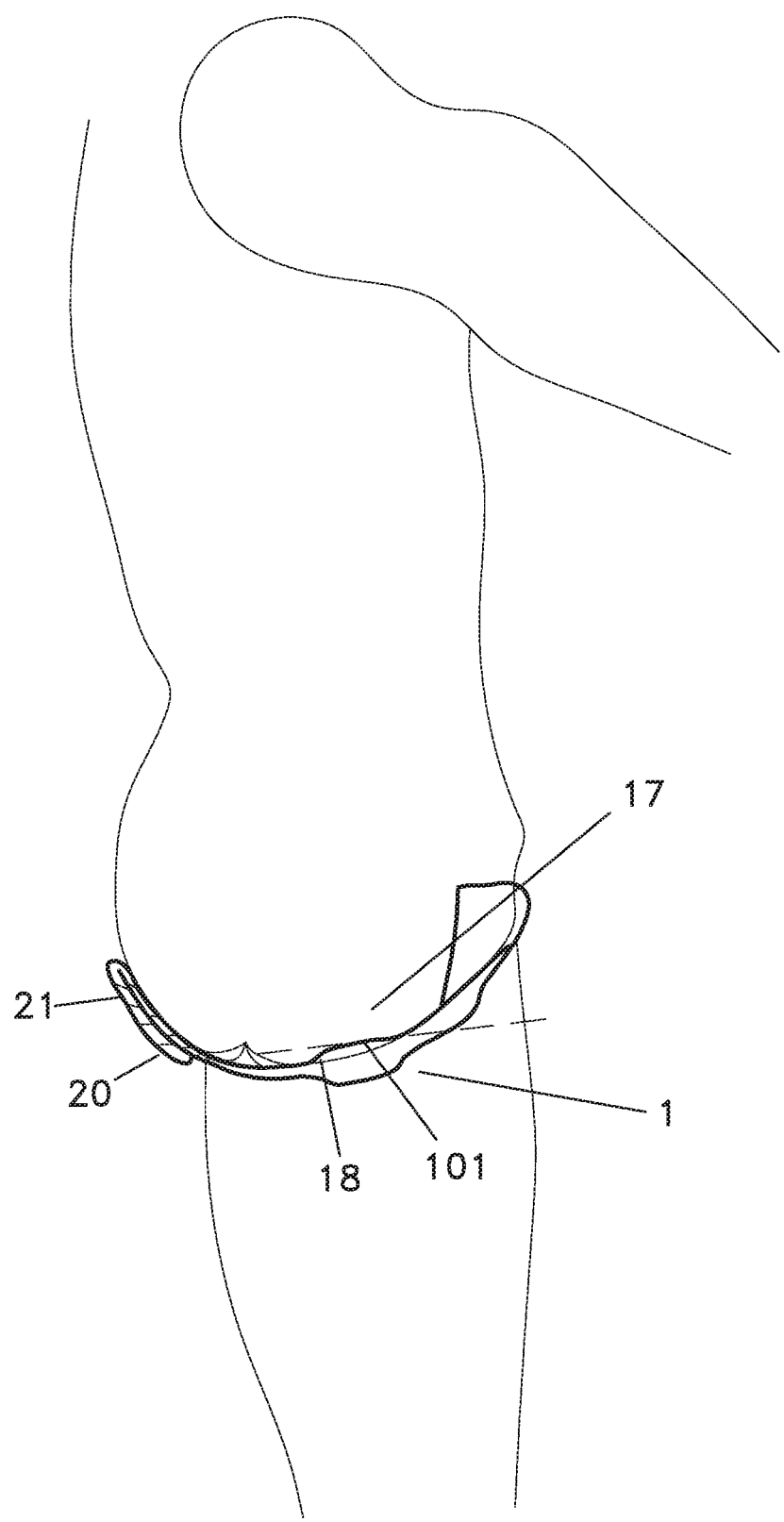
FIG. 19 shows a mid-sagittal plane view cross-section of an embodiment of an inventive pad while being worn by a male. Note that profiles of a buttock, leg, shoulder and arm, while not visible in a pure mid-sagittal plane view, are nonetheless shown for clarity of presentation to the viewer and to help orient the viewer. Note also that the bulge appearing at the bottom of the pad is "push-out" of the ridge as it is forced against skin of the wearer.
Figure 20:
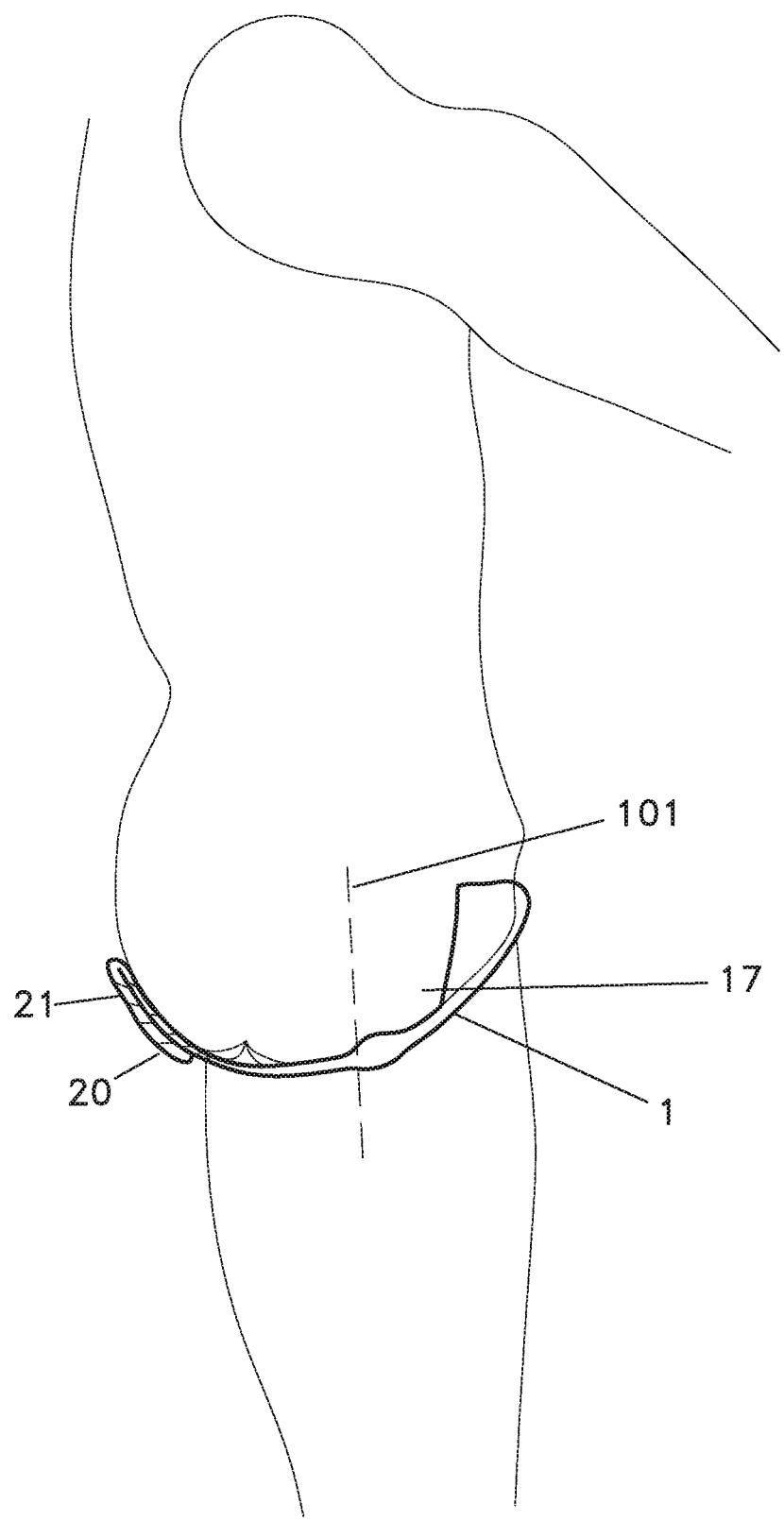
FIG. 20 shows a mid-sagittal plane view cross-section of an embodiment of an inventive pad while being worn by a female. As with FIG. 19, the profiles of a buttock, leg, shoulder and arm, while not visible in a pure mid-sagittal plane view, are nonetheless shown for clarity of presentation to the viewer and to help orient the viewer. Note also that the bulge appearing at the bottom of the pad is "push-out" of the projection as it is forced against skin of the wearer.
Figure 21:
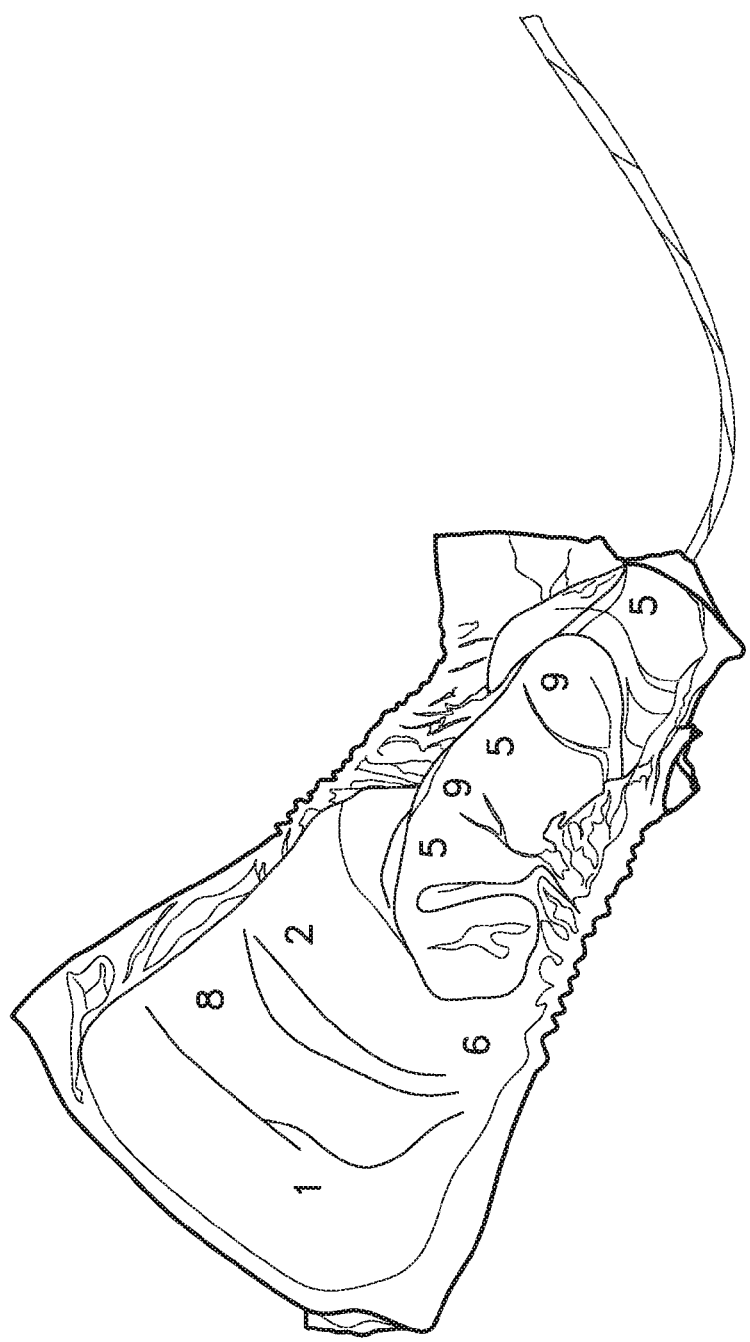
FIG. 21 shows a left side perspective view photograph of an embodiment of an inventive pad featuring a raised ridge and a manually graspable cord.
Figure 22:
FIG. 22 shows a right side perspective view photograph of an embodiment of an inventive pad featuring a raised ridge and a manually graspable cord.

While, in general, fabricating a raised ridge may be performed by the pre-purchase manufacturer, or by the post-purchase user, certain embodiments are particularly amenable to fabrication of the raised ridge by the user him or herself. More particularly, in certain embodiments, the raised ridge may be fabricated from a conventional, readily available incontinence pad that, at purchase, does not feature a raised ridge. The raised ridge can be fabricated by exposing adhesive that maybe on the exterior of the pad (conventionally intended to secure the pad to undergarment (e.g., underwear) worn just outside of the pad), and manually forming the raised ridge. See generally FIGS. 18A and 18B. Applied pressure from the side of the raised ridge should secure opposing sides to each other, thereby forming the raised ridge on a side opposite the adhesive. In certain embodiments, a portion of a cord may be placed along part of the longitudinal centerline of the pad before parts of the opposing sides of the pad are brought together to form the ridge; the ridge can then be formed around the cord portion (with a remaining portion extending and exposed posteriorly of the raised ridge) by laterally applying opposing pressure (e.g., horizontally, from the left and the right, towards a plane that includes the longitudinal center of the pad) to the raised ridge, thereby adhering opposite sides to each other, and securing the cord portion within the ridge such that pulling on its remaining exposed portion (typically extending in a posterior direction) applies force to the raised ridge (see generally, FIGS. 18A and 18B). Once formed, the cord can run within and along the length of the raised ridge (whether along the entire length, or along only a portion of the length, such as one half, one third, two thirds, three fourths, etc.). The anterior portion (approximately ½, for example) of the pad can be formed (e.g., via pushing the outside of a cupped hand or first against such portion) into a pouch, or pocket. The converted pad can then be placed, for use, such that the raised ridge 5 is below the perineum of the user; remaining adhesive (if it exists) on the external and front side of the pad may be secured to a garment worn outside of the pad, thereby securing the pad in position. [It is of incidental note that in any embodiment of the inventive technology disclosed herein, adhesive (on the external, garment proximate side of the pad) may be used to adhere the pad to an undergarment worn outside of the pad.] Accordingly, certain embodiments of the inventive technology may include a kit that enables purchasers to form the raised ridge. The kit could include instructions (see above) and perhaps a cord (in addition, perhaps, to a pad). It would enable a user to convert a conventional pad he or she has purchased so as to have a pad that has a raised ridge, and possibly also a cord that can be used to apply force to the raised ridge (and thus to a urethra of the user). Note that where the raised ridge (or, more generally, projection) is formed by a manufacturer prior to sale, the projection may be folded up 180 degrees into the upper pouch; the two can them be folded together from the right and left sides, and perhaps held there via tape, forming a compact package for sale.

More particularly as to materials, in certain embodiments, the step of fabricating the base may comprise the step of fabricating the base from a first material (e.g., absorbent fabric) and wherein the step of fabricating the raised ridge may comprise the step of fabricating the raised ridge at least in part from the first material. In such embodiments, an inner, skin proximate portion of the base and an inner, skin proximate portion of the raised ridge may be different portions of the same perhaps layered, sheet-like material. In particular designs, the raised ridge may comprise a comparatively more rigid support component 13 that provides support for it; such comparatively more rigid support component may established below the same layered, sheet like material (in those designs where at least part of the raised ridge and part of the base are of the same material. In other embodiments, the step of fabricating the raised ridge may comprise the step of fabricating a raised ridge that is a discrete component from the base but that is attached to the base.

Regardless of whether the raised ridge and the pad base are made from the same material or are discrete components, the step of fabricating the raised ridge 5 may comprise the step of establishing as part of the raised ridge a comparatively more rigid material 13 that provides support for the raised ridge. Such comparatively more rigid material may comprise a material selected from the group consisting of foam, plastic, cord and cardboard. As to those aspects of fabrication that relate to the length, shape and height of the raised ridge, the inventive technology should be understood to also include any steps of fabricating the raised ridge to have any of the aforementioned, apparatus type length, shape and height features. For example, as there is mention of a cord 20 that may be attached to the raised ridge, this specification should also be understood to include disclosure of fabricating a raised ridge that has a cord attached thereto.

An aspect of the inventive technology may be described as an incontinence pad that comprises: an absorbent pad base 2 (which includes, but is not limited to, a partially absorbent pad base) having an outer surface 3 capable of being established against clothing of a user when the pad is worn by the user; an inner surface 6 that is on a side of the pad that is opposite the outer surface (e.g., and against skin of a user while the pad is worn thereby); and a cord 20 forming part of and attached to the pad. Note that only part of a pad base need be absorbent for it to be an absorbent pad base (although indeed substantially all of it may be absorbent). Further, the cord is the to form part of the pad only by virtue of its connection thereto (i.e., the cord may appear as an attached, accessory item to the pad and still be part of the pad).

Note that in certain embodiments, the cord 20 is attached along at least a portion of a centerline 4 defined by the incontinence pad (where the centerline lies in a mid-sagittal plane of a wearer of the pad, and may divide the pad into right and left halves). The cord 20 may have a manually graspable portion 21 (i.e., that portion of the cord that may be manually grasped by a user thereof); it may be substantially at a longitudinal end (e.g., a posterior end) of the pad. The cord may include an additional cord portion 33 attached to the manually graspable cord portion 21 and forming part of the cord, where at least part of the additional cord portion is established between the outer surface and the inner surface, and substantially along at least part of a longitudinal pad centerline that lies substantially within a mid-sagittal plane of the user when the incontinence pad is worn thereby. In particular embodiments, the additional cord portion may be established between the inner surface and the outer surface. It may be established substantially along a longitudinal pad centerline 4 that lies substantially within a mid-sagittal plane of the user when the incontinence pad is worn thereby. In certain embodiments, at least a portion of the cord extends posteriorly beyond a posterior end of the pad. During wearing of the pad, the at least a portion of the cord that extends posteriorly may drape or hang vertically downward posteriorly of the pad, or it may extend upward (e.g., if it is stiff enough, as is the case with certain paper cord). In certain other embodiments (e.g., those offering directional bias), none of the cord may extend posteriorly beyond a posterior end of the pad. Note also that the cord may form a loop (perhaps for easy grasping . . . note that a cord is deemed grasped even where it has a loop that is hooked with a finger). The loop may be substantially at a posterior end of the cord. As mentioned, the loop may be manually graspable.

In certain embodiments there may be provided a bias element 30 configured to act on the cord. The bias element may bias the cord in a tensile direction. While a bias element may be found only in particular embodiments, in those where it does exist, it may be part of a cord (as where that part is elastic). It may eliminate or reduce the need to manually grasp and tug at the cord to secure the pad in proper position, particularly when the cord is attached at both ends to the pad. Note that a bias element may even find application where there is a manually graspable cord portion, as the manually graspable cord portion may supplement the action of the bias element (in securing the pad in proper position, e.g., securing a raised ridge thereof in the intergluteal cleft of the user). In preferred embodiments, the cord has a longitudinal front end and a longitudinal rear end and the bias element is substantially at one of the ends. As mentioned, in certain embodiments, both ends of the cord may be attached to the pad (e.g., to a raised ridge thereof, and/or to the base thereof, as but two examples).

In particular embodiments, the cord may be attached to the pad (i.e., any part thereof) at a cord attachment site 31, which may be substantially at a posterior end of the pad, substantially at an anterior end of the pad, or somewhere therebetween (although typically it will be attached to a posterior portion of the pad (i.e., posterior of a mid-coronal plane of a user wearing the pad)). In embodiments with a raised ridge, the site may be a portion of the raised ridge interior, or all of the raised ridge interior. Attachment can be achieved in any number of ways—seamless "meshing" of the cord into the pad (e.g., into a raised ridge of the pad), hook and loop fastener, adhesive, sewing and stitching, tying, to name a few). In certain preferred embodiments, the cord attachment site is within (on) a longitudinal pad centerline 4 that lies substantially within a mid-sagittal plane of the user when the incontinence pad is worn thereby. More particularly as to the cord itself, it can be a type of rope, twine, tether, cloth, nylon, fibrous material, cotton material, absorbent material, elastic, rubber, paper cord and mesh rope, as but a few examples.

As mentioned, certain pad embodiments—including those with a cord—may include a raised ridge established above part of the base and having a surface that is established against at least a portion of the perineum of the user when the incontinence pad is worn by the user. The raised ridge itself may define a raised ridge centerline 32 that lies substantially within the mid-sagittal plane of the user when the incontinence pad is worn by the human user. In such embodiments, a cord may be attached to the raised ridge. The cord may include a manually graspable portion 21 and an additional cord portion 33, wherein at least part of the additional cord portion may be established between the outer surface 3 and the inner surface 6, and substantially along at least part of a longitudinal pad centerline that lies substantially within a mid-sagittal plane of the user when the incontinence pad is worn thereby. In certain embodiments, at least part of the additional cord portion 33 is established substantially under the raised ridge 5. Optionally, at least part of the additional cord portion forms at least part of the raised ridge, and perhaps this cord portion is a support for the raised ridge (or the part that is above this cord portion). In these and other embodiments, the additional cord portion (or part thereof) may be between the inner surface and the outer surface of the pad.

Particular embodiments of the inventive technology may include a short length projection 35 configured to apply pressure to a urethra of a user. Such short length projection may be particularly useful in an incontinence pad designed for women, as the urethra of women does not pass above the perineum, but instead travels essentially straight down to a urethral opening site in the vagina. As such, the short length projection (e.g, a bulb), when properly situated, may apply a force that acts substantially along a longitudinal axis of the urethra, at the urethral opening (including in the area of the clitoris, labium majora and/or labium minora). Typically, the short length projection is smaller in front to back length than any raised ridge (e.g., it may be less than two inches in length, less than one inch in length, less than ¾ inch in length) and have a width (in a coronal plane) that is small enough to avoid interference with inner thighs on either side. In such a pad, a cord 20 may be attached to the short length projection; such cord, whether it has a manually graspable portion or a biased portion (or both), may operate (or be operable) to apply the aforementioned upward force. In certain embodiments, the short length projection, when properly situated and a design force is applied (perhaps along a cord and/or as a result of sitting), may obstruct flow (at least partially) via simple physical obstruction at the urethral opening. Note that such design force (i.e., a force sufficient to achieve the desired urinary flow mitigation) may be applied via manual operation of a cord attached (either directly or indirectly) to the short length projection (short length front to back), via a bias element 30 that is part of a cord so attached, by sitting and/or by tight fitting clothing. Indeed, the very mechanisms of application of a design force/pressurization to a raised ridge may also be found to apply a design force in any embodiment. It should be understood that the upward, short length projection may also find application in a male incontinence pad, but in the male version, the projection would be established so that when the pad is worn, it is below a perineum of the user and can apply pressure thereagainst (in order to pressurize the urethra passing above it). As such, and as with other embodiments of the inventive technology, the pad may, but need not, be designed for a particular gender (i.e., one model may be intended specifically for a woman, and have a short length projection located so that, during wearing of the pad by a woman, it is just below a urethral opening, and another model may be intended specifically for a man, with a short length projection positioned so that, during wearing of the pad by a male, the projection is below the perineum of a user.) Note that a projection may be long enough (i.e., it might not be a short length projection) or it may be a short length projection that can be positioned properly (whether by positioning of the entire pad relative to the bodily coverage area or via removal of the projection from the pad and repositioning of the projection on the pad as is appropriate) such that it "fits" or can be adjusted to fit both male and female users (e.g., in a woman, at least part of the projection is below the urethral opening and in an male at least part of the projection is below the perineum).

At least one embodiment of the inventive technology may be described as a method to mitigate incontinence comprising the steps of establishing a pad having an absorbent pad base 2 and an inner surface 6; establishing at least part of the inner surface adjacent a perineum of the user; and directionally biasing (whether manually, via manual grasping and pulling a manually graspable cord portion upward/outward; and/or through operation of a bias element (e.g., of a cord)) at least a portion of the pad by a cord 20 attached to and forming part of the pad. Accordingly, such biasing may include the step of directionally biasing with a cord that is attached to the pad at a cord attachment site 31 (e.g., that may be within (along part of) a longitudinal pad centerline 4 defined by the pad and that lies substantially within a mid-sagittal plane of the user when the incontinence pad is worn thereby).

More particularly as to the step of directionally biasing, such step may comprise directionally biasing with a cord that has a manually graspable portion, in an upward and/or outward direction. Such cord portion may be substantially at a longitudinal end of the pad. The cord may further include an additional cord portion established between the manually graspable cord portion 21 and a cord end. The manually graspable cord portion may be substantially at a posterior end of the pad; it may, in certain embodiments, form a loop, which may be substantially at a posterior end of the manually graspable cord portion.

As mentioned, the step of directionally biasing may comprise the step of directionally biasing with a cord 20 that further comprises an additional cord portion 33 proximal the manually graspable cord, at least part of the additional cord portion being established between the outer surface 3 and the inner surface 6, and substantially along at least part of a longitudinal pad centerline 4 that lies substantially within a mid-sagittal plane of the user when the incontinence pad is worn thereby. The additional cord portion 33 may be established between the inner surface and the outer surface. It may be established substantially along a longitudinal pad centerline 4 that lies substantially within a mid-sagittal plane of the user when the incontinence pad is worn thereby. In certain embodiments, at least a part of the manually graspable cord portion 21 extends posteriorly beyond a posterior end 15 of the pad. In such embodiments, during wearing of the pad, the at least a part of the manually graspable cord portion that extends posteriorly may draper vertically downward posteriorly of the pad. However, in other embodiments, none of the cord extends posteriorly beyond a posterior end 15 of the pad.

Figure 16A:
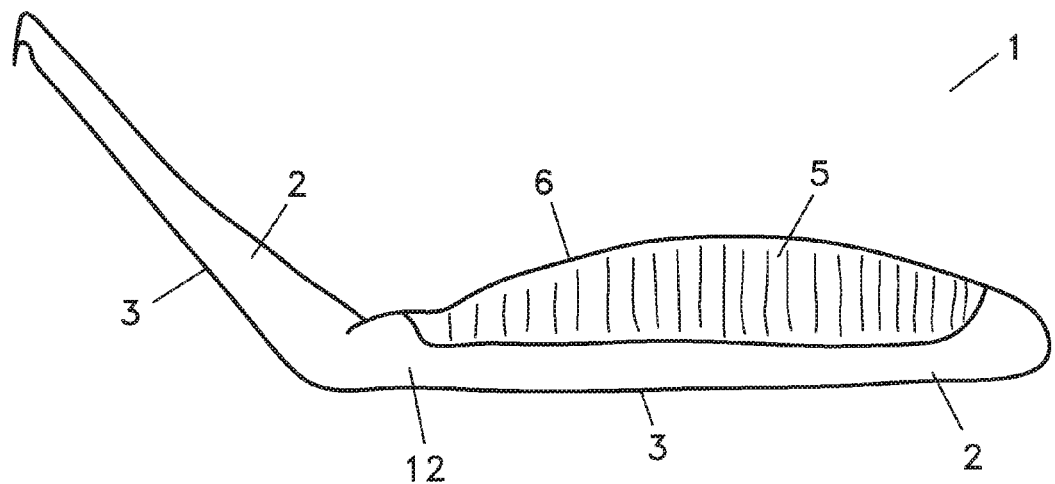
FIG. 16A shows a longitudinal cross-section (cut into equal right and left halves down a longitudinal axis defined by the pad) view drawing of an embodiment of an incontinence pad featuring a substantially longitudinal absorbency separator.
Figure 16B:
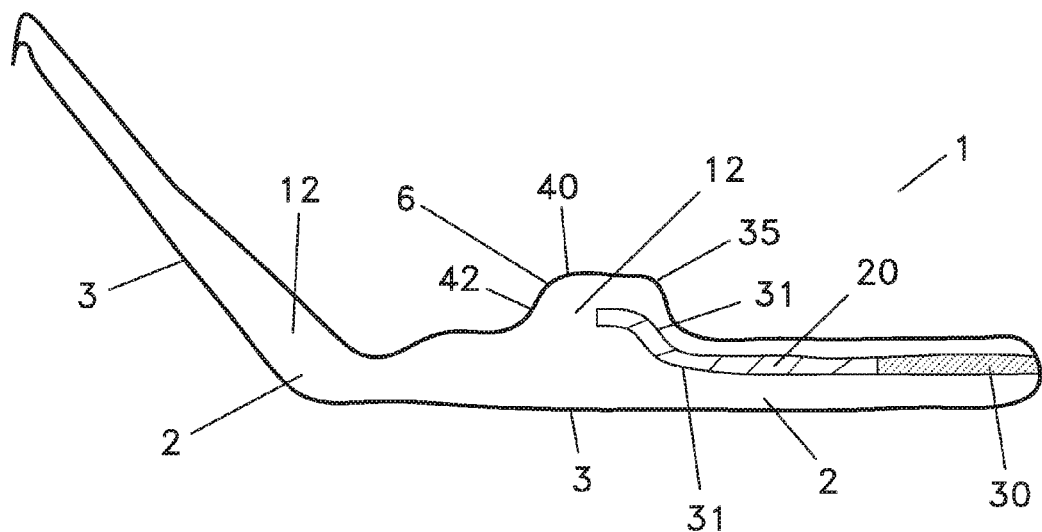
FIG. 16B shows a longitudinal cross-section view drawing of an embodiment of an incontinence pad featuring a cord without a manually graspable portion (but with a bias element).
Figure 17A:
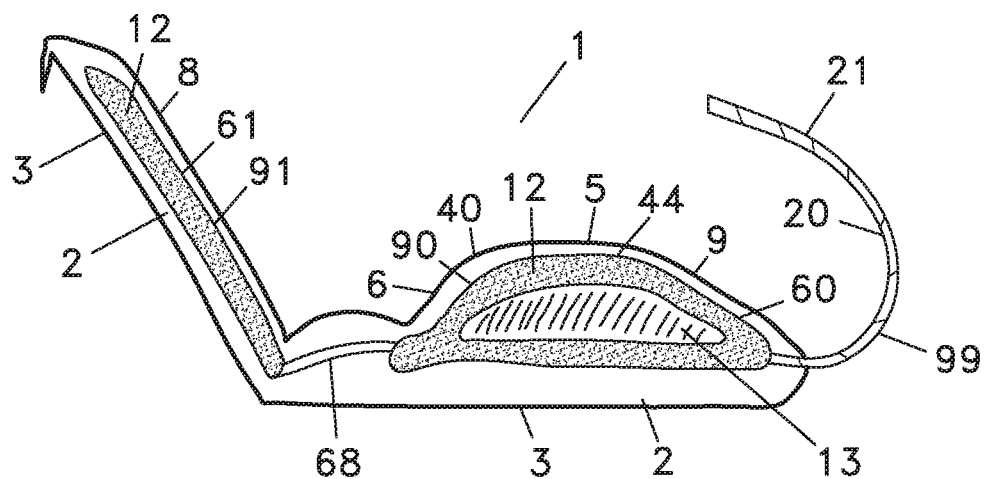
FIG. 17A shows a longitudinal cross-section view drawing of an embodiment of an incontinence pad featuring a comparatively more rigid support for the raised ridge, and a compressible support area absorbent portion, an overflow absorbent portion, and a fluidic communicator therebetween.
Figure 17B:
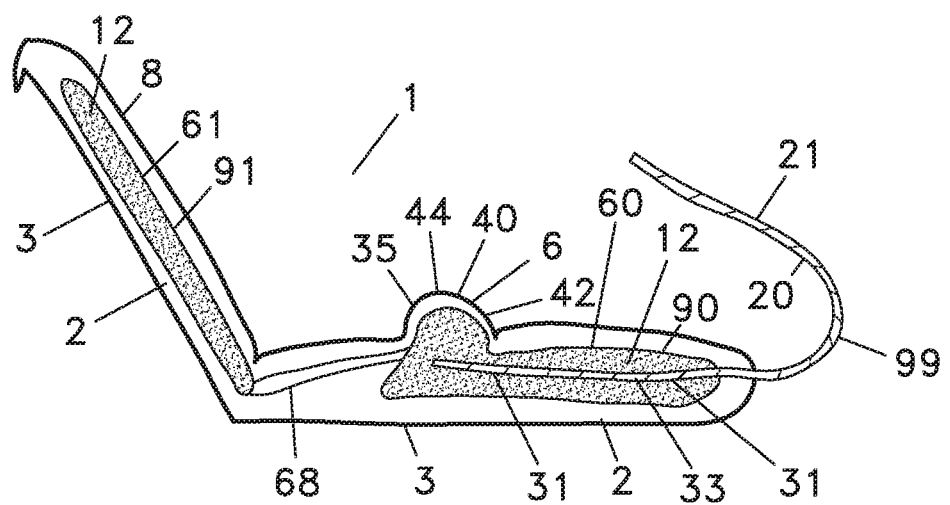
FIG. 17B shows a longitudinal cross-section view drawing of an embodiment of an incontinence pad featuring a short length projection, and a compressible support area absorbent portion, an overflow absorbent portion, and a fluidic communicator therebetween.

Regardless of whether any cord includes a manually graspable portion 21, the step of directionally biasing may include the step of directionally biasing at least in part through action of a bias element 30 that biases the cord in a tensile direction. This bias element may be part of any manually graspable cord portion 21 that exists (although it need not), part of an additional cord portion 22, or, it can be part of a cord that does not have a portion that is intended for intentional manual grasping for application of a design force (see FIG. 16B, note that in such designs, both ends may be attached to the pad, although this is not necessarily a required feature, with a bias element therebetween). Accordingly, in certain embodiments, the bias element may be the to be part of the cord (and such part may be elastic). The cord, likely having a longitudinal front end and a longitudinal rear end, may have a bias element substantially at one end, and, as explained, both of the ends may be attached to the pad (e.g., to a pad base (or other pad component, such as a raised ridge)).

As mentioned, method embodiments that involve a pad with a cord (and those without a cord, of course) may involve a pad that includes a raised ridge 5. As such, the pad (pad apparatus) may further comprise a raised ridge established above part of the base and having a surface that is established against at least a portion of the perineum of the user when the incontinence pad is worn by the user, the raised ridge itself defining a raised ridge centerline 32 that lies substantially within the mid-sagittal plane of the user when the incontinence pad is worn by the human user. The cord may be attached to the raised ridge; it may include a manually graspable portion 21 and an additional cord portion 22, wherein at least part of the additional cord portion may be established between the outer surface 3 and the inner surface 6, and substantially along at least part of a longitudinal pad centerline 4 that lies substantially within a mid-sagittal plane of the user when the incontinence pad is worn thereby. It is of note that at least part of the additional cord portion may be established substantially under the raised ridge. Regardless, at least part of the additional cord portion may form at least part of the raised ridge. Such at least part of the additional cord portion may form a support for the raised ridge; it may be between the inner surface of the pad and the outer surface of the pad.

Embodiments of the "directionally biasing" methods of the inventive technology may further comprise the step of configuring a short length projection 35 to apply pressure to a urethra of the user. A cord may be attached to the short length projection 35; in certain embodiments, it may be particularly suited for use as part of an incontinence pad designed for women (e.g., as a result of its placement relative to the rest of the pad, and/or its size (as where it is small enough to apply pressure at the urethral opening).

Note that in certain embodiments, pressure against the urethra (whether applied via a projection 50 or a raised ridge 5, or at the urethral opening or at the perineum) may initially be created by manually pulling a manually graspable cord 99 (or as manually graspable cord portion 21 thereof) that is attached (perhaps via an additional cord portion) to the pad, raised ridge, or projection, and pulling (upward and/or outward), then securing the raised ridge (e.g., securing into position via action of the buttocks on either side of the intergluteal cleft). In certain embodiments, such pressurization may be maintained (partially or entirely) via a bias element 30 (e.g., an elastic band) that, when the uppermost, rear portion of the pad is brought (e.g., likely by manually grasping it or a cord attached to part of it) to an intended, proper wearing height, applies force to the raised ridge and/or projection that, like a cord that is wrapped around a cylinder and then pulled, applies an inward force onto the cylinder. In certain embodiments, the raised ridge 5 may play a role in maintaining such force, in that it may be established it in the intergluteal cleft during a tensioning/pulling of the raised ridge into such cleft (where it is then, after any manual release of the pad, secured through action of the buttocks moving horizontally towards each other). Note that these mechanisms of applying force may be supplemented or supplanted by sitting and/or tight fitting briefs (which, by the way, can act alone, e.g., in embodiments without a cord or a raised ridge, thereby replacing any manually initiated/generated pressurization). Note that because a posterior portion (or even an anterior portion) of the pad can also be grasped, some embodiments may eliminate the cord, while still allowing for manual establishment of the raised ridge into the intergluteal cleft. Preferably, but not necessarily, any cord may exit the pat substantially at a posterior portion of the pad (in other embodiments, the manually graspable cord portion may be at the anterior pad portion). It is also of note that certain embodiments, as mentioned, may rely only on pressurization (at the projection) created during sitting and/or tight fitting briefs. This is in keeping with the fact that any of the various independent aspects of the inventive technology disclosed herein (including but not limited to the raised ridge, the upward, short length projection, the cord, the bias element, the absorbency separator, the secondary retention element, etc.) may be featured alone or in any sort of combination or permutation.

Particular apparatus embodiments may be described as an incontinence pad 1 that includes a base 2 having an outer surface 3 capable of being established against clothing of a user when the incontinence pad is worn by the user; a targeted pressure element 40 established above at least a portion of the base; and an absorbent established adjacent skin of the user when the incontinence pad is worn by the user. The absorbent maybe at least a portion of the base and/or targeted pressure element. The targeted pressure element may be a raised ridges (particularly, but not exclusively, where it's configured to pressurize the urethra of a male) and/or an upward, short length projection 42 (particularly, but not exclusively, where it is pressurized to pressurize the urethra of female). In certain embodiments, when it is a raised ridge, it may effect pressure that acts transverse to a longitudinal axis 101 of the urethra (where that axis is defined by the male urethra in the area of the perineum and the female urethra in the area of the urethral opening). When it's an upward, short length projection, it may effect pressurization that acts in a direction that is substantially along the long (longitudinal) axis of the urethra (of a female); it may be configured for establishment directly below a urethral opening of a female wearing the pad. However, an upward, short length projection may be used on a male, and a raised ridge may used on a female.

A related method to mitigate incontinence may be described as comprising the steps of: establishing an absorbent pad 1 in a genital area 17 of a user (e.g., as by "putting on" the pad); creating a targeted pressure increase at a targeted location (e.g., a perineum of a male, or a urethral opening on a female) on the user through action of the absorbent pad (perhaps by sitting, by the action of tight fitting clothing worn around the pad, by manual operation of a graspable cord portion (and perhaps also retention of part of the pad, such as a raised ridge, in the intergluteal cleft of a pad wearer), and/or by action of a bias element); and absorbing at least a substantial portion of any emissions from the user as a result of the incontinence within the absorbent pad. Accordingly, the step of creating a targeted pressure increase may comprise the step of creating a targeted pressure increase through action of a raised ridge 5 of the pad and/or through action of a upward, short length projection 42 of the pad. Note that the step of creating a targeted pressure increase at a targeted location may comprise the step of creating a targeted pressure increase at a perineum of a user (typically of a male user, although a raised ridge may also be effective in applying pressure to the urethral opening of females, and thus useful for mitigating incontinence of women). Aforementioned specifics regarding such pressure may also apply here. Note also that, particularly as to females, the step of creating a targeted pressure increase at a targeted location may comprise the step of creating a targeted pressure increase at a urethral opening of a user. As mentioned, this may be accomplished (at least in part) through action of an upward, short length projection of the pad.

Particular embodiments of the inventive technology may be described as an incontinence pad that comprises a pad 1, itself comprising an absorbent pad base 2, the pad having an outer surface 3 capable of being established against clothing of a user when the pad is worn by the user; an inner surface 6 of the pad, the inner surface opposite the outer surface; a urethral compressor 44 (e.g., a raised ridge, or an upward, short length projection) attached to the pad along at least a portion of the inner surface; and an absorbent established adjacent skin of the user when the incontinence pad is worn by the user. The urethral compressor may be configured to pressure the urethra of a male, particularly where the wearer is a male (pressure effected by the urethral compressor may act transverse to a longitudinal axis of the urethra). In certain embodiments, the urethral compressor may be configured to pressure the urethra of a female (e.g., as where it is an upward, short length projection and pressure effected by the urethral compressor acts substantially along a longitudinal axis of the urethra). Particularly with women, the urethral compressor may be configured for establishment directly below a urethral opening of a female wearing the pad so it can create pressure at such opening (note that as to pads having a raised ridge, a portion of the raised ridge may be below a urethral opening of a male, but such is not intended to create pressure at such opening (as indeed, with males, the incontinence mitigation preferably occurs via pressurization of the urethra applied at the perineum)).

A method to mitigate incontinence comprising the steps of: establishing an absorbent pad 1 in a genital 17 area of a user; creating urethral compression at a location on the user through action of the absorbent pad; and absorbing at least a substantial portion of any emissions (e.g., urine) from the user as a result of the incontinence within the absorbent pad. Note that the step of creating urethral compression may comprise the step of doing so through action of a raised ridge, an upward, short length projection, a bias element, tight fitting clothing around the pad, and/or through the act of sitting. Note that the step of establishing an absorbent pad in a genital area of a user may comprise the step of establishing an absorbent pad in the genital area of a female or male user, and that either a raised ridge or an upward, short length projection, can be effective for either if properly situated as part of the pad (e.g., the raised ridge, for women, should pass under the urethral opening, and for men, the upward, short length projection should be established under the perineum of the male). However, it may be that the raised ridge is more effective for men, and the upward, short length projection, with its more targeted pressurization, is more effective for women. Nonetheless, use of the upward, short length projection may be somewhat effective for men also, and use of the raised ridge may be somewhat effective for women. Note also that a primary difference between the raised ridge and the upward, short length projection may be the front to back length of each (the upward short length projection may have a shorter length, and may to apply a more targeted, focused pressurization). The raised ridge, while critically, in certain male pad embodiments, applying a force to the perineum (a term that includes applying a force merely to a portion thereof), may be longer not so that it can apply pressure elsewhere, but instead perhaps so that such raised ridge can be established and secured in the intergluteal cleft of a user, thereby keeping the raised ridge taut from front to back, and thereby keeping the perineum pressurized (and the urethra above it).

It is of note that, even in embodiments with an upward, short length projection, there may also be a raised ridge; it would typically be separated from the short length projection. Such raised ridge in such embodiments, may, primarily, be intended for establishment in an intergluteal cleft (and securing therein), thereby keeping a perineum (male) or urethral opening (female) pressurized.

Particular embodiments may be described as a an incontinence pad comprising an absorbent pad base, the pad base having an outer surface capable of being established against clothing of a user when the pad is worn by the user; an inner surface of the pad, the inner surface opposite the outer surface; a nerve trigger element 49 (attached to the pad and forming part thereof) along at least a portion of the inner surface; and an absorbent established adjacent skin of the user when the incontinence pad is worn by the user. The nerve trigger can be a raised ridge or an upward, short length projection. It may affect a parasympathetic nerve, perhaps upon compressing it, perhaps effecting constriction (or tightening) of a urethral sphincter.

A related method to mitigate incontinence may be described as comprising the steps of: establishing an absorbent pad in a genital area of a user; triggering at least one nerve reaction through action of the absorbent pad; and absorbing at least a substantial portions of any emissions from the user as a result of the incontinence within the absorbent pad. The step of triggering may comprise the step of triggering at least one nerve reaction through compressive action, which may be effected by a raised ridge or an upward, short length projection, sitting or by tight fitting clothing. The nerve reaction may be a parasympathetic nerve reaction; such reaction may effect tightening of a urethral sphincter.

Another set of embodiments related to an independent aspect of the inventive technology may be described generally as an incontinence pad 1 comprising: an outer surface 3 capable of being established against clothing of a user when the pad is worn by the user, the pad also defining a centerline 4; an absorbent 45 (e.g., an fluid absorbent fabric, absorbent layered material, absorbent material, etc.) established adjacent skin of the user when the pad is worn by the user; and a substantially longitudinal absorbency separator 46 configured within at least a portion of the absorbent along the centerline. The substantially longitudinal absorbency separator may be established substantially along at least part of a longitudinal centerline 4 of the pad (in the mid-sagittal plane defined by a wearer of the pad), perhaps within the absorbent (meaning either entirely within it or only partially with it); it may be longer from front to back than it is wide (from right to left). It may serve to prevent the flow of retained (absorbed) fluid from a right side of the absorbent to a left side of the absorbent; in that sense it may be a sort of liquid flow blocking wall that may divide the absorbent into two sections (right and left sections 52, 53, perhaps equal in size). It may also possibly serve to divert fluid into a right or left absorbent portion shortly after emission thereof. Whether the fluid retention component that is separated is a projection, raised ridge, or other component (including a pad base), it may, in certain embodiments, equalize left and right fill amounts, thereby maximizing the total retention capacity before leakage or overflow therefrom occurs. It may form part of (be within) and/or be below a portion of or all of any raised ridge or projection that may be present. Any cord or bias element may be attached to it, although this is certainly optional and not a necessary feature of apparatus featuring a cord and/or bias element. It may have a variety of lengths to achieve its intended purpose, from substantially a posterior end of the pad to an anterior end of the pad, to much shorter. While it certainly may have some structural rigidity to it (such may also provide structure for any raised ridge that may exist), it may also or instead be compressible (e.g., for comfort during sitting).

A related set of method type embodiments of the inventive technology intended to mitigate incontinence may comprise the steps of: establishing a pad 1 having a centerline 4 in a genital area of a user (upon a user "putting on" the pad); establishing an absorbent 45 adjacent skin of the user (which may also be accomplished when the user "puts on" the pad); absorbing at least a substantial portions of any emissions from the user as a result of the incontinence within the absorbent (which may occur shortly after a urinary emission while wearing the pad); and substantially longitudinally separating absorption within the absorbent along at least a portion of the centerline (which may be achieved whenever flow is intentional prevented from crossing from a right side of the absorbent to a left side, or vice versa). The step of substantially longitudinally separating absorption may comprise separating with a liquid flow blocking wall 51, perhaps with one that is established from a posterior end of the pad to an anterior end (although other lengths are contemplated as being within the ambit of the inventive technology). Of course, features specified immediately above relative to the apparatus version of the flow separator technology also apply to the method version.

Another independent aspect of the inventive technology disclosed herein may be described as an incontinence pad that comprises: an absorbent pad base that has an outer surface capable of being established against clothing of a user when the pad is worn by the user, the absorbent base having a centerline; an inner surface that is opposite the outer surface; and a substantially perpendicular structure 54 attached to the pad and forming a portion of the inner surface along the centerline. This perpendicular structure could be a raised ridge or, in other embodiments, a projection. While in certain embodiments, the perpendicular structure has substantially vertical sides when the pad is worn by a user, this is not a requirement, as the term perpendicular refers to the following feature: when viewed in a cross-sectional plane that is transverse to a mid-sagittal plane, that intersects the perpendicular structure, and that includes a normal vector that proceeds from the top of the perpendicular structure and that points in towards the pad wearer, the perpendicular structure defines a centerline that is perpendicular to a baseline between the two sides (right/left) of the lower part of the pad in that cross-sectional plane. In particular embodiments, the perpendicular structure (in the aforementioned cross-sectional plane) has sides that are not substantially vertical but instead slope upwards from the pad on both right and left sides of the perpendicular structure.

A related procedure to mitigate incontinence may be described as comprising the steps of: establishing a pad having an absorbent pad base and an inner surface in a genital area of a user; establishing a portion of the inner surface adjacent a perineum of the user; and interposing a substantially perpendicular structure 54 (e.g., a raised ridge, a raised, short length projection) along at least a portion of the inner surface in the vicinity of at least a portion of the perineum of the user. The term perpendicular is as defined immediately above, in the description of the related apparatus. Further, the sides of the perpendicular structure may be vertical or upwardly sloping, as described above relative to the related apparatus version.

Another independent aspect of the inventive technology may be described as an incontinence pad that comprises: a primary fluid retention element 60 (e.g., as may be found in a pad base, or a raised ridge, for example) having an outer surface 3 capable of being established against clothing of a user when the incontinence pad is worn by the user, the primary retention element having a centerline (front to back, or longitudinal); a locationally separate secondary fluid retention element 691 established adjacent the user on at least a portion of the centerline; and an inner surface 6 opposite the outer surface 3 capable of being established adjacent skin of the user when the incontinence pad is worn by the user. Note that the locationally separate secondary fluid retention element may be at least part of a raised ridge absorbent, or part even of an upward, short length projection (as in the case where the primary retention element is part of the pad base) or, instead, at least a portion of the pad base. It may define a centerline that is established substantially along at least a portion of a longitudinal centerline (e.g., within a mid-sagittal plane of a wearer) defined by the pad. The locationally separate secondary fluid retention element may be established (e.g., during wearing of the pad) between a base fluid retention element and skin of a wearer of the pad, or it may be part of the base (i.e., it may be a base fluid retention element). Note also that the primary fluid retention element may be divided into substantially two halves by a substantially longitudinal absorbency separator. It may comprise a base fluid retention element, or a perineum area retention element 67 (such as a raised ridge retention element). The primary fluid retention element is wherever the fluid is first retained (even if only momentarily) before it (or some of it) is conveyed to the locationally separate secondary fluid retention element. Such conveyance may occur, in at least one embodiment, when a certain amount of fluid is input into the primary fluid retention element. At such point, fluid may be transferred to the locationally separate secondary fluid retention element. This conveyance may occur via what may be referred to as a fluidic communicator 68 (e.g., a pathway). It may be established to fluidically communicate the primary fluid retention element with the locationally separate secondary fluid retention element. In such manner, when one retention element is full (or reaches a certain level or amount), it can overflow into the other. Such conveyance may occur via, e.g., wicking, pressurization and/or gravitationally. Similarly, when one is compressed (which happens often with the primary retention element), instead of some fluid retained therein perhaps being forced out of the pad entirely, such fluid instead may be fluidically communicated (moved via flow) to the other retention element. The fluidic communicator may be, as but a few examples, a permeable material (e.g., a fluid permeable fabric), a channel, a pathway, and a tube (e.g., a straw-like tube). It may be the same material as the primary fluid retention element and/or the locationally separate secondary fluid retention element (and may even have similar dimensions (e.g., same thickness and/or right to left width) as the primary fluid retention element and/or the locationally separate secondary fluid retention element. Fluid permeable material may achieve fluid conveyance via wicking, and/or pressure (e.g., from the front to the back of the pad (e.g., to a pad cup), where pressure is applied from sitting, for example), and/or gravitationally. Wicking may also be simply a result of gravitational force (where the initial emission is in a forward "pocket", and such fluid may be passed through gravitational force and/or wicking to a retention area (e.g., a projection such as a raised ridge) that may be towards the rear of the pad. Note that, in certain embodiments, the retention element towards the front of the pad may be referred to as a forward absorptive pocket 69 (in which the penis and scrotum may rest).

A related method to mitigate incontinence may comprise the steps of: retaining fluid within a primary fluid retention element positioned substantially at a genital area of a user; and locationally separately secondarily retaining fluid adjacent the user. Retaining fluid within a primary fluid retention element may be achieved by retaining fluid within a pad base absorbent, or instead, e.g., within a raised ridge. The step of locationally separately secondarily retaining fluid adjacent the user may be achieved by retaining fluid within a raised ridge absorbent and/or a projection absorbent (e.g., absorbent within or of a raised ridge or an upward, short length projection), but in those embodiments where the primary retention element is the raised ridge absorbent, the secondary retention element would be the pad base (including e.g., a pad cup, which would be towards the front of the pad and would be shaped (whether before or during use), to cup male genitalia during use; the cup may, but need not be of the same length as any raised ridge that may exist). The method may further comprise the step of separating absorbed fluid into right and left fluid retention portions; this may be done in absorbent of the pad base and/or of the raised ridge absorbent via the aforementioned substantially longitudinal absorbency separator. Of course, the step of locationally separately secondarily retaining fluid adjacent the user may comprise the step of locationally separately secondarily retaining fluid within a locationally separate secondary fluid retention element (e.g., a pad base, or a pad cup, as in the case where the primary retention element is the raised ridge). Note that inventive methods may further comprise the step of fluidically communicating the primary fluid retention element to the locationally separate secondary fluid retention element (by providing for conveyance of fluid from the primary fluid retention element to the locationally separate secondary fluid retention element). Note that the primary fluid retention element is that part of the pad that tends to retain most of the fluid that is first expelled into a pad during an incontinence event.

Another independent aspect of the inventive technology may be described as an incontinence pad that comprises: a base retention element 71 having an outer surface capable of being established against clothing of a user when the incontinence pad is worn by the user, the base retention element having a centerline; a separate perineum retention element 67 established above part of the retention element along at least a portion of the centerline; and an inner surface opposite the outer surface capable of being established adjacent skin of the user when the incontinence pad is worn by the user. The separate perineum retention element may comprise (e.g., be part of, or be entirely within, or be partly within or be one and the same as) a urethral compressor, a raised ridge, a projection, and/or a targeted pressure element. It is intended to be substantially below the perineum; for this reason it is typically found in an incontinence pad that is specifically designed for a male, but may also be found in gender inspecific pads, or pads designed for women (typically pads designed for women would have a projection in the area of the urethral opening). In particular embodiments, either the base retention element or the perineum retention element is the primary retention element. There may be a fluidic communicator between the two retention elements.

Related method embodiments to mitigate incontinence comprise the steps of: retaining fluid within a primary retention element positioned at a genital area of a user; and separately secondarily retaining fluid (e.g., within a perineum area of a user, or within a base retention element). The method may further comprise the step of compressing a urethra of a user. This may be accomplished, for a male or a female, in any of the various manners mentioned elsewhere in this disclosure.

As mentioned, particular embodiments of the inventive technology may include a short length projection (protruding upwards). Such embodiments may be described as an incontinence pad comprising: an absorbent pad base, the pad having an outer surface capable of being established against clothing of a user when the pad is worn by the user and defining a centerline 4; an inner surface on a side of the pad that is opposite the outer surface; and a short length projection 35 along at least a portion of the centerline and configured for positioning at a location below a urethra of the user user to mitigate at least some effects of incontinence. In such embodiments, the short length projection is smaller in front to back length than any raised ridge (e.g., it may be less than two inches in length, less than one inch in length, less than ¾ inch in length) and has a width (in a coronal plane) that is small enough to avoid interference with inner thighs of the user on either side of the pad. In certain embodiments that are more geared towards women, the short length projection is configured (including placed relative to the rest of the pad) so that it is directly below a urethral opening. In other embodiments (i.e., those that are more designed for men), it may be configured so that, during wearing of the pad, the short length projection is below a urethra as it passes above a perineum of the male user. In either case, it may be intended to pressurize the urethra via any of the several mechanisms described elsewhere herein. Note that the short length projection may have any of a variety of shapes—substantially frustoconical, substantially conical, substantially pyramidal, substantially block-shaped, substantially-rectangular shaped, and substantially hemispherical in shape, as but a few examples. Note that it, like any of the other projections articulated herein (raised ridge, e.g.), can be repositioned on the pad base (e.g., by a user, to "customize" the location for a specific user in order, for example, to achieve improved pressurization of the urethra (at the opening or transversely, as described) as intended or desired. One of the many ways in which the projection can be repositioned (detached and then re-secured/re-attached) is via adhesive or hook and loop fastener (e.g., the loop side may be along a portion of the pad base (along a longitudinal centerline) that is longer (front to back) than the front to back length of the projection, and the underside of the projection may have a hook portion attached to it).

Related inventive technology to mitigate incontinence may be described as a method comprising the steps of: manufacturing a pad to have an absorbent pad base and an inner surface in a genital area of a user; manufacturing a short length projection so that it is adjacent a urethra of the user; and absorbing at least a substantial portions of any emissions from the user as a result of the incontinence within the absorbent pad base. The short length projection may, and typically does, project upwards (such that it is an upward, short length projection). In pads designed for women, a short length projection may be configured (located on the pad and/or sized) for positioning (by a user) at a location below a urethral opening of the user so that a force is applied to the urethral opening; in pads designed for men, a short length projection may be designed for positioning at a location below the perineum (or, more particularly, below a urethra as it passes above a perineum) of the user. In either case, the step of manufacturing a short length projection may be the to comprise the step of step of manufacturing a short length projection to apply pressure to the urethra (e.g., during sitting, by tight fitting clothing, through operation of a cord and/or bias element (e.g., elastic band)). As the projection (particularly when of short length) may be any of a variety of shapes (including but not limited to frustoconical, cylindrical, conical, pyramidal, block like, of oval, circular or rectangular base, etc.), the step of manufacturing may include the step of manufacturing a short length projection that is any of these shapes. Further, the step of manufacturing may include the step of manufacturing a short length projection that is repositionable on the absorbent pad base; it may be repositionable on the absorbent pad base via hook and loop fastener.

Particular embodiments of the inventive technology may be described as an incontinence pad that comprises: a compressible support area absorbent portion having 90 an outer surface capable of being established against clothing of a user when the incontinence pad is worn by the user and an inner surface capable of being established against a skin surface of the user when the incontinence pad is worn by the user; an overflow absorbent portion 91 established adjacent the compressible support area absorbent portion; a fluidic communicator 68 fluidically connecting (e.g., via liquid permeable fabric (allowing one-way or two-way fluid passage), cord, foam, material in the form of a pathway, channel, fluid conveyor, channel, conduit, etc.) the compressible support area absorbent portion and the overflow absorbent portion; and a connection element connecting the compressible support area absorbent portion and overflow absorbent portion (where the term portion here implies that each absorbent portion is but a part of the entire absorbent of the pad). Note that the overflow absorbent portion, in certain embodiments, may be a type of secondary fluid retention element. The fluidic communicator may allow for conveyance of overflow from one retention element (e.g. from the compressible support area absorbent portion) to the other (even where the first is not completely filled with fluid, as overflow includes flow from an absorbent that is first to retain fluid to an absorbent that is next to retain fluid, regardless of at which level (amount of retained fluid in the first absorbent) such flow starts). Similarly, when one is compressed (which happens often with the primary retention element or the compressible support area absorbent portion), instead of some fluid retained therein perhaps being forced out of the pad entirely, such fluid instead may be fluidically communicated (moved via flow) to the other retention element (e.g. to the overflow retention element). Note that compressible support area absorbent portion may comprise an intergluteal cleft area absorbent portion and/or a perineum area absorbent portion. The connection element may be the fluidic communicator or at least form part of it or include it. As mentioned, the fluidic communicator is at least partially fluid permeable (it may also be at least partially absorbent). It may be made from (by example) cotton, fibrous material, cloth, layered material, synthetic material and natural material. The compressible support area absorbent portion of the pad may be compressed when a user of the pad sits on a surface (such compression may pressurize that pad portion and force fluid materials retained in it outward). As mentioned, the fluidic communicator may be configured to allow passage of at least some fluid absorbed in the compressible support area absorbent portion from the compressible support area absorbent portion to the overflow absorbent portion; fluid so passed may be overflow of the compressible support area absorbent portion. Note that in certain embodiments, the fluidic communicator allows for two-way fluid passage (such that overflown fluid can return to its initial retained location (e.g., the compressible support area absorbent portion) after the compressive force is disapplied), while in others it may allow for only one-way passage. The connector may be an integral connector (e.g., made from the same material as that at least one of the connected parts), fibrous connector, thread connector, stitching connector and adhesive connector, as but a few examples. Such connection may be a portion of the overflow absorbent portion, or may perhaps be along an entire length of the overflow absorbent portion. Note that the compressible support area absorbent portion may comprise a raised ridge and/or an upward projection (as but two examples) the overflow absorbent may be more anteriorly disposed. Both of the compressible support area absorbent portion and the overflow absorbent portion may both be fluid retentive.

A related method, to mitigate fluid leakage from an incontinence pad, the pad defining an enclosed space between the pad and skin of a wearer of the pad, may be described as comprising the steps of: retaining fluid within a compressible support area absorbent portion positioned at a genital area of a user; establishing a overflow absorbent portion adjacent the compressible support area absorbent portion; and mitigating (e.g., reducing) through action of the overflow absorbent portion, a tendency of the compressible support area absorbent portion to expel some of the retained fluid from the enclosed space upon compression of the compressible support area absorbent portion. The step of mitigating comprises the step of conveying the some of the retained fluid from the compressible support area absorbent portion to the overflow absorbent portion; such step may take place when external pressure is applied to the compressible support area absorbent portion (e.g., from sitting, including sitting down, and moving while sitting). During such step of pressurization, the conveying may be of some of the retained fluid during overflow from the compressible support area absorbent portion; it may include the step of conveying the some of the retained fluid through a fluidic communicator fluidically connecting the compressible support area absorbent portion and the overflow absorbent portion. In such manner, expelled fluid may be retained in the overflow absorbent portion. As alluded to above, the step of establishing an overflow absorbent portion may comprise the step of establishing a intergluteal cleft area absorbent portion, establishing a perineum area absorbent portion, establishing a raised ridge absorbent portion, and establishing a projection absorbent portion, establishing an anterior pocket area absorbent portion, establishing a posterior absorbent portion, establishing an anterior absorbent portion, and establishing a central absorbent portion.

However, in other embodiments, the overflow absorbent portion is within an intergluteal cleft absorbent, a raised ridge, a perimeum area absorbent, or a projection. The compressible support area could be, e.g. on either/both sides of the intergluteal cleft, or more towards the front of the pad.

Clauses

The following clauses describe the various aspects of the inventive technology, in embodiments. Note that any of the indicated limitations, whether disclosed in the clauses below, in the description, and/or in the figures, may describe various aspect(s) of the inventive technology either alone or with any one or more other limitations.

1. An incontinence pad comprising:
    a base having an outer surface capable of being established against clothing of a user when said incontinence pad is worn by said user, with said base having a centerline;
    a raised ridge established above part of said base on at least a portion of said centerline; and
    an inner surface capable of being established adjacent skin of said user when said incontinence pad is worn by said user.
2. An incontinence pad as described in clause 1, or any other clause, wherein said inner surface comprises a base inner surface and a raised ridge inner surface.
3. An incontinence pad as described in clause 1, or any other clause, wherein said outer surface comprises a liquid impermeable outer surface.
4. An incontinence pad as described in clause 1, or any other clause, wherein said outer surface comprises an outer layer.
5. An incontinence pad as described in clause 4, or any other clause, wherein said outer layer comprises a liquid impermeable outer layer.
6. An incontinence pad as described in clause 1, or any other clause, wherein said inner surface comprises a one-way liquid impermeable inner surface.
7. An incontinence pad as described in clause 1, or any other clause, wherein said base comprises a liquid absorbent material.
8. An incontinence pad as described in clause 1, or any other clause, wherein at least part of said base and at least part of said raised ridge are of the same material.
9. An incontinence pad as described in clause 8, or any other clause, wherein an inner, skin proximate portion of said base and an inner, skin proximate portion of said raised ridge are different portions of the same layered, sheet like material.
10. An incontinence pad as described in clause 9, or any other clause, wherein said raised ridge comprises a comparatively more rigid support component that provides support for it.
11. An incontinence pad as described in clause 10, or any other clause, wherein said comparatively more rigid support component is established below said same layered, sheet like material.
12. An incontinence pad as described in clause 1, or any other clause, wherein said base and said raised ridge are discrete pad components.
13. An incontinence pad as described in clause 1, or any other clause, wherein said raised ridge comprises a comparatively more rigid material that provides support for it.

14. An incontinence pad as described in clause 13, or any other clause, wherein said comparatively more rigid material comprises a material selected from the group consisting of foam, plastic and cardboard.
15. An incontinence pad as described in clause 1, or any other clause, wherein said raised ridge has one end that terminates substantially at a longitudinal end of said pad and another end that terminates at a non-end portion of said pad.
16. An incontinence pad as described in clause 15, or any other clause, wherein said end of said raised ridge that terminates substantially at a longitudinal end of said pad is a posterior end of said raised ridge.
17. An incontinence pad as described in clause 1, or any other clause, wherein a posterior end of said raised ridge terminates in the intergluteal cleft of a user when said pad is worn by said user.
18. An incontinence pad as described in clause 17, or any other clause, wherein said posterior end of said raised ridge terminates in the intergluteal cleft, below the anus of a user when said pad is worn by said user.
19. An incontinence pad as described in clause 18, or any other clause, wherein a posterior end of said pad terminates higher than does said posterior end of said raised ridge of said pad, when said pad is worn by said user.
20. An incontinence pad as described in clause 1, or any other clause, wherein said raised ridge has a cross-sectional shape in a coronal plane when worn by a user that is selected from the group of shapes consisting of: triangular, half-circular disc shaped, block shape and chamfered edge block shape.
21. An incontinence pad as described in clause 1, or any other clause, wherein said raised ridge has a front end to rear end length that is less than a front end to rear end length of a length of a typical said perineum.
22. An incontinence pad as described in clause 1, or any other clause, wherein said raised ridge has a front end to rear end length that is greater than or substantially the same as a front end to rear end length of a typical said perineum.
23. An incontinence pad as described in clause 1, or any other clause, wherein said raised ridge is positioned on said base portion such that at least part of said raised ridge is established under said perineum during use of said pad by said user.
24. An incontinence pad as described in clause 1, or any other clause, wherein said raised ridge is configured to apply a flow blocking pressure to said urethra of said user during use of said pad by said user, when said user is in a seated position.
25. An incontinence pad as described in clause 24, or any other clause, wherein a height, shape and stiffness of said raised ridge are sufficient to apply said flow blocking pressure to said urethra of said user during use of said pad by said user, when said user is in a seated position.
26. An incontinence pad as described in clause 25, or any other clause, wherein said height, shape and stiffness of said raised ridge, and tightness of clothing worn around said pad, are sufficient to apply said flow blocking pressure to said urethra of said user during use of said pad by said user, when said user is in a non-seated position.
27. A method to mitigate incontinence comprising the steps of:
    establishing an absorbent pad in a genital area of a user;
    establishing a raised ridge adjacent a perineum of said user; and
    absorbing at least a substantial portion of any emissions from said user as a result of said incontinence within said absorbent pad.
28. The method as described in clause 27, or any other clause, further comprising applying localized pressure to the perineum of said user at least partially through use of said raised ridge of said pad.
29. The method as described in clause 28, or any other clause, further comprising compressing the urethra of said user with said localized pressure.
30. The method as described in clause 29, or any other clause, further comprising preventing said involuntary urination.
31. The method as described in clause 27, or any other clause, wherein said step of applying localized pressure comprises the step of applying pressure exerted from under said raised ridge by a sitting surface in response to sitting by said user on said surface.
32. The method as described in clause 27, or any other clause, wherein said step of applying localized pressure comprises the step of exerting pressure by briefs that are tight fitting.
33. The method as described in clause 27, or any other clause, wherein said step of applying localized pressure comprises the step of applying pressure through action of a cord that may be attached to the raised ridge.
34. The method as described in clause 27, or any other clause, further comprising the step of securing said pad in position.
35. The method as described in clause 34, or any other clause, wherein said step of securing said pad is achieved at least in part by compressing part of said pad in the intergluteal cleft through use of a user's buttocks' bias towards each other.
36. The method as described in clause 35, or any other clause, wherein said step of compressing part of said pad comprises the step of compressing said raised ridge.
37. The method as described in clause 36, or any other clause, wherein said raised ridge is a portion of a pad that also comprises a base.
38. The method as described in clause 34, or any other clause, wherein said step of securing said pad in position comprises the step of manually grasping a manually graspable cord attached to said pad and pulling said cord upward and back.
39. The method as described in clause 38, or any other clause, wherein said cord is attached to at least a portion of said pad that is along a longitudinal centerline of said pad
40. A method of fabricating an incontinence item, or any other clause, wherein said incontinence item comprises a base and a raised ridge element that has a centerline, said method comprising the steps of:
    fabricating said base, said base having at least a portion that is absorbent and having a centerline; and
    fabricating said raised ridge element to be positioned along at least a portion of said centerline of said base.
41. The method as described in clause 40, or any other clause, wherein said step of fabricating said raised ridge element comprises the step of fabricating said raised ridge element to be detachable from said base.
42. The method as described in clause 41, or any other clause, wherein said step of fabricating said raised ridge element to be detachable from said base comprises the step of fabricating said raised ridge element to be detachable from said base with hook and loop fastener.

43. The method as described in clause 41, or any other clause, wherein said step of fabricating said raised ridge element to be detachable from said base comprises the step of fabricating said raised ridge element to be re-attachable to said base.

44. The method as described in clause 43, or any other clause, further comprising the step of fabricating said raised ridge element to be repositionable on said base.

45. The method as described in clause 40, or any other clause, further comprising configuring so the raised ridge element has a centerline that lies substantially within the mid-sagittal plane of a user of said pad.

46. The method as described in clause 40, or any other clause, further comprising configuring so while said user of said pad is in a seated position, said raised ridge applies a pressure to the perineum of said user, said pressure sufficient to obstruct involuntary urine flow through said urethra.

47. The method as described in clause 40, or any other clause, wherein said step of fabricating said raised ridge comprises the step of fabricating said raised ridge by adhering right and left side portions of said base to each other.

48. The method as described in clause 47, or any other clause, further comprising the step of placing a portion of a cord along at least a portion of said centerline of said base before performing said step of fabricating said raised ridge.

49. The method as described in clause 40, or any other clause, wherein said step of fabricating said raised ridge comprises the step of fabricating said raised ridge so that, while said pad is worn by a user, a posterior portion of said raised ridge is established in the intergluteal cleft of said user.

50. The method as described in clause 49, or any other clause, wherein said step of fabricating comprises the step of fabricating said raised ridge so that a posterior end of said raised ridge terminates in the intergluteal cleft, below the anus of a user when said pad is worn by said user.

51. The method as described in clause 50, or any other clause, wherein said step of fabricating said base comprises the step of fabricating said base so that said posterior end of said pad terminates higher than does said posterior end of said raised ridge, when said pad is worn by said user.

52. The method as described in clause 40, or any other clause, wherein said step of fabricating said base comprises the step of fabricating said base from a first material and, or any other clause, wherein said step of fabricating said raised ridge comprises the step of fabricating said raised ridge at least in part from said first material.

53. The method as described in clause 52, or any other clause, wherein an inner, skin proximate portion of said base and an inner, skin proximate portion of said raised ridge are different portions of the same layered, sheet like material.

54. The method as described in clause 53, or any other clause, wherein said raised ridge comprising comparatively more rigid support component that provides support for it.

55. The method as described in clause 54, or any other clause, wherein said comparatively more rigid support component is established below said same layered, sheet like material.

56. The method as described in clause 40, or any other clause, wherein said step of fabricating said raised ridge comprises the step of fabricating a raised ridge that is a discrete component from said base but that is attached to said base.

57. The method as described in clause 40, or any other clause, wherein said step of fabricating said raised ridge comprises the step of fabricating a raised ridge that is, at least in part, a different portion of the same material that makes up at least part of said base.

58. The method as described in clause 40, or any other clause, wherein said step of fabricating said raised ridge comprises the step of establishing as part of said raised ridge a comparatively more rigid material that provides support for said raised ridge.

59. The method as described in clause 58, or any other clause, wherein said comparatively more rigid material comprises a material selected from the group consisting of foam, plastic, cord and cardboard.

60. The method as described in clause 40, or any other clause, wherein said step of fabricating said raised ridge comprising the step of fabricating said raised ridge to have a posterior end that terminates below the anus of a user.

61. The method as described in clause 40, or any other clause, wherein said step of fabricating said raised ridge comprising the step of fabricating said raised ridge to have an anterior end that terminates posteriorly of the scrotum of a user and substantially at the anterior end of the perineum of said user.

62. The method as described in clause 40, or any other clause, wherein said step of fabricating said raised ridge comprising the step of fabricating said raised ridge to have a posterior end that terminates within the intergluteal cleft of a user.

63. The method as described in clause 40, or any other clause, wherein said step of fabricating said raised ridge comprising the step of fabricating said raised ridge to have a cross-sectional shape in a coronal plane when worn by a user, or any other clause, wherein said cross-sectional shape is selected from the group of shapes consisting of: triangular, half-circular disc shaped, block shape and chamfered edge block shape.

64. The method as described in clause 40, or any other clause, wherein said step of fabricating said raised ridge comprising the step of fabricating said raised ridge to have a front end to rear end length that is less than a front end to rear end length of a typical length of said perineum.

65. The method as described in clause 40, or any other clause, wherein said step of fabricating said raised ridge comprising the step of fabricating said raised ridge to have a front end to rear end length that is greater than a front end to rear end length of a typical length of said perineum.

66. The method as described in clause 40, or any other clause, wherein said step of fabricating said raised ridge comprising the step of fabricating said raised ridge so that said raised ridge is positioned on said base such that at least part of said raised ridge is established under said perineum during use of said pad by said user.

67. The method as described in clause 40, or any other clause, wherein said step of fabricating said raised ridge comprising the step of fabricating said raised ridge to apply a flow blocking pressure to said urethra of said user during use of said pad by said user, when said user is in a seated position.

68. The method as described in clause 67, or any other clause, wherein a height, shape and stiffness of said raised ridge are sufficient to apply said flow blocking pressure to said urethra of said user during use of said pad by said user, when said user is in a seated position.
69. The method as described in clause 40, or any other clause, wherein said step of fabricating said raised ridge comprising the step of fabricating said raised ridge so that urethra pressure affecting factors are sufficient to apply said flow blocking pressure to said urethra of said user during use of said pad by said user, when said user is in a non-seated position.
70. The method as described in clause 40, or any other clause, wherein said urethra pressure affecting factors are selected from the group consisting of: raised ridge height, raised ridge shape, raised ridge stiffness, tightness of clothing worn around said pad, retention of said pad within an intergluteal cleft of said user.
71. An incontinence pad comprising:
an absorbent pad base having an outer surface capable of being established against clothing of a user when said pad is worn by said user;
an inner surface that is on a side of said pad that is opposite said outer surface; and
a cord forming part of and attached to said pad.
72. An incontinence pad as described in clause 71, or any other clause, wherein said inner surface is established against skin of said human user when said incontinence pad is worn thereby.
73. An incontinence pad as described in clause 71, or any other clause, wherein said cord is attached along at least a portion of a centerline defined by said incontinence pad.
74. An incontinence pad as described in clause 71, or any other clause, wherein said cord has a manually graspable portion.
75. An incontinence pad as described in clause 74, or any other clause, wherein said manually graspable cord portion is substantially at a longitudinal end of said pad.
76. An incontinence pad as described in clause 75, or any other clause, wherein said manually graspable cord portion is substantially at a posterior end of said pad.
77. An incontinence pad as described in clause 74, or any other clause, further comprising an additional cord portion attached to said manually graspable cord portion and forming part of said cord, at least part of said additional cord portion established between said outer surface and said inner surface, and substantially along at least part of a longitudinal pad centerline that lies substantially within a mid-sagittal plane of said user when said incontinence pad is worn thereby.
78. An incontinence pad as described in clause 77, or any other clause, wherein said additional cord portion is established between said inner surface and said outer surface.
79. An incontinence pad as described in clause 77, or any other clause, wherein said additional cord portion is established substantially along a longitudinal pad centerline that lies substantially within a mid-sagittal plane of said user when said incontinence pad is worn thereby.
80. An incontinence pad as described in clause 74, or any other clause, wherein at least a portion of said cord extends posteriorly beyond a posterior end of said pad.
81. An incontinence pad as described in clause 74 w, during wearing of said pad, said at least a portion of said cord that extends posteriorly extends upwardly posteriorly of said pad base.
82. An incontinence pad as described in clause 74, or any other clause, further comprising an additional cord portion established proximal said manually graspable cord portion.
83. An incontinence pad as described in clause 71, or any other clause, wherein none of said cord extends posteriorly beyond a posterior end of said pad.
84. An incontinence pad as described in clause 71, or any other clause, wherein said cord forms a loop.
85. An incontinence pad as described in clause 84, or any other clause, wherein said loop is substantially at a posterior end of said cord.
86. An incontinence pad as described in clause 85, or any other clause, wherein said loop is manually graspable.
87. An incontinence pad as described in clause 71, or any other clause, further comprising bias element configured to act on said cord.
88. An incontinence pad as described in clause 87, or any other clause, wherein said bias element biases said cord in a tensile direction.
89. An incontinence pad as described in clause 87, or any other clause, wherein said bias element is part of said cord.
90. An incontinence pad as described in clause 89, or any other clause, wherein at least part of said cord is elastic.
91. An incontinence pad as described in clause 87, or any other clause, wherein said cord has a longitudinal front end and a longitudinal rear end.
92. An incontinence pad as described in clause 91, or any other clause, wherein said bias element is substantially at one of said ends.
93. An incontinence pad as described in clause 91, or any other clause, wherein both of said ends are attached to said pad.
94. An incontinence pad as described in clause 71, or any other clause, wherein said cord is attached to said pad at a cord attachment site.
95. An incontinence pad as described in clause 94, or any other clause, wherein said cord attachment site is substantially at a posterior end of said pad.
96. An incontinence pad as described in clause 94, or any other clause, wherein said cord attachment site is substantially at an anterior end of said pad.
97. An incontinence pad as described in clause 94, or any other clause, wherein said cord attachment site is within a longitudinal pad centerline that lies substantially within a mid-sagittal plane of said user when said incontinence pad is worn thereby.
98. An incontinence pad as described in clause 71, or any other clause, wherein said cord is selected from the group consisting of rope, twine, tether, cloth, nylon, fibrous material, cotton material, absorbent material, mesh rope, elastic, rubber, and paper cord.
99. An incontinence pad as described in clause 71, or any other clause, further comprising raised ridge established above part of said base and having a surface that is established against at least a portion of the perineum of said user when said incontinence pad is worn by said user, said raised ridge itself defining a raised ridge centerline that lies substantially within said mid-sagittal plane of said user when said incontinence pad is worn by said human user.
100. An incontinence pad as described in clause 99, or any other clause, wherein said cord is attached to said raised ridge, within said raised ridge.
101. An incontinence pad as described in clause 99, or any other clause, wherein said cord comprises a manually graspable portion and an additional cord portion, or any other clause, wherein at least part of said additional cord portion is established between said outer surface and said inner surface, and substantially along at least part of a longitudinal pad centerline that lies substantially within a mid-sagittal plane of said user when said incontinence pad is worn thereby.

102. An incontinence pad as described in clause 101, or any other clause, wherein at least part of said additional cord portion is established substantially under said raised ridge.

103. An incontinence pad as described in clause 101, or any other clause, wherein at least part of said additional cord portion forms at least part of said raised ridge.

104. An incontinence pad as described in clause 103, or any other clause, wherein said at least part of said additional cord portion forms part of said raised ridge, and said at least part of said additional cord portion forming part of said raised ridge is a support for said raised ridge.

105. An incontinence pad as described in clause 101, or any other clause, wherein said additional cord portion is attached to said pad at a cord attachment site.

106. An incontinence pad as described in clause 105, or any other clause, wherein said cord attachment site is at an end portion of said pad.

107. An incontinence pad as described in clause 101, or any other clause, wherein said additional cord portion is between said inner surface and said outer surface.

108. An incontinence pad as described in clause 71, or any other clause, further comprising a short length projection configured to apply pressure to a urethra of said user.

109. An incontinence pad as described in clause 108, or any other clause, wherein said cord is attached to said short length projection.

110. An incontinence pad as described in clause 108, or any other clause, wherein said cord is manually graspable.

111. An incontinence pad as described in clause 108, or any other clause, wherein said short length projection is substantially frusto-conical shaped.

112. A method to mitigate incontinence comprising the steps of:
establishing a pad having an absorbent pad base and an inner surface;
establishing at least part of said inner surface adjacent a perineum of said user; and
directionally biasing at least a portion of said pad by a cord attached to and forming part of said pad.

113. A method as described in clause 112, or any other clause, wherein said step of directionally biasing comprises the step of directionally biasing with a cord that is attached to said pad at a cord attachment site.

114. A method as described in clause 113, or any other clause, wherein said cord attachment site is substantially at a posterior end of said pad.

115. A method as described in clause 113, or any other clause, wherein said cord attachment site is substantially at an anterior end of said pad.

116. A method as described in clause 113, or any other clause, wherein said cord attachment site is within a longitudinal pad centerline that lies substantially within a mid-sagittal plane of said user when said incontinence pad is worn thereby.

117. A method as described in clause 112, or any other clause, wherein said step of directionally biasing comprises the step of directionally biasing with a cord that is attached along at least a portion of a centerline defined by said incontinence pad.

118. A method as described in clause 112, or any other clause, wherein said step of directionally biasing comprises the step of directionally biasing with a cord that has a manually graspable portion.

119. A method as described in clause 118, or any other clause, wherein said manually graspable cord portion is substantially at a longitudinal end of said pad.

120. A method as described in clause 119, or any other clause, further comprising an additional cord portion established between said manually graspable cord portion and a cord end.

121. A method as described in clause 118, or any other clause, wherein said manually graspable cord portion is substantially at a posterior end of said pad.

122. A method as described in clause 118, or any other clause, wherein said manually graspable cord portion forms a loop.

123. A method as described in clause 122, or any other clause, wherein said loop is substantially at a posterior end of said manually graspable cord.

124. A method as described in clause 118, or any other clause, wherein said step of directionally biasing comprises the step of directionally biasing with a cord that further comprises an additional cord portion proximal said manually graspable cord, at least part of said additional cord portion established between said outer surface and said inner surface, and substantially along at least part of a longitudinal pad centerline that lies substantially within a mid-sagittal plane of said user when said incontinence pad is worn thereby.

125. A method as described in clause 124, or any other clause, wherein said additional cord portion is established between said inner surface and said outer surface.

126. A method as described in clause 124, or any other clause, wherein said additional cord portion is established substantially along a longitudinal pad centerline that lies substantially within a mid-sagittal plane of said user when said incontinence pad is worn thereby.

127. A method as described in clause 118, or any other clause, wherein at least a part of said manually graspable cord portion extends posteriorly beyond a posterior end of said pad.

128. A method as described in clause 118, or any other clause, wherein during wearing of said pad, said at least a part of said manually graspable cord portion that extends posteriorly drapes vertically downward posteriorly of said pad.

129. A method as described in clause 112, or any other clause, wherein none of said cord extends posteriorly beyond a posterior end of said pad.

130. A method as described in clause 112, or any other clause, wherein said step of directionally biasing comprises the step of directionally biasing at least in part through action of a bias element that biases said cord in a tensile direction.

131. A method as described in clause 130, or any other clause, wherein said bias element is part of said cord.

132. A method as described in clause 131, or any other clause, wherein at least part of said cord is elastic.

133. A method as described in clause 130, or any other clause, wherein said cord has a longitudinal front end and a longitudinal rear end.

134. A method as described in clause 133, or any other clause, wherein said bias element is substantially at one of said ends.

135. A method as described in clause 133, or any other clause, wherein both of said ends are attached to said pad.

136. A method as described in clause 112, or any other clause, wherein said cord is selected from the group consisting of rope, twine, tether, cloth, nylon, fibrous material, cotton material, absorbent material, mesh rope, elastic, rubber, and paper cord.

137. A method as described in clause 112 a, or any other clause, further comprising raised ridge established above part of said base and having a surface that is established against at least a portion of the perineum of said user when said incontinence pad is worn by said user, said raised ridge itself defining a raised ridge centerline that lies substantially within said mid-sagittal plane of said user when said incontinence pad is worn by said human user.

138. A method as described in clause 137, or any other clause, wherein said cord is attached to said raised ridge.

139. A method as described in clause 137, or any other clause, wherein said cord comprises a manually graspable portion and an additional cord portion, or any other clause, wherein at least part of said additional cord portion is established between said outer surface and said inner surface, and substantially along at least part of a longitudinal pad centerline that lies substantially within a mid-sagittal plane of said user when said incontinence pad is worn thereby.

140. A method as described in clause 139, or any other clause, wherein at least part of said additional cord portion is established substantially under said raised ridge.

141. A method as described in clause 139, or any other clause, wherein at least part of said additional cord portion forms at least part of said raised ridge.

142. A method as described in clause 139, or any other clause, wherein said at least part of said additional cord portion forms part of said raised ridge, and said at least part of said additional cord portion forming part of said raised ridge is a support for said raised ridge.

143. A method as described in clause 139, or any other clause, wherein said additional cord portion is between said inner surface and said outer surface.

144. A method as described in clause 112, or any other clause, further comprising the step of configuring a short length projection to apply pressure to a urethra of said user.

145. A method as described in clause 144, or any other clause, wherein said cord is attached to said short length projection.

146. A method as described in clause 144, or any other clause, wherein said short length projection is substantially frusto-conical shaped.

147. An incontinence pad comprising:
a base having an outer surface capable of being established against clothing of a user when said incontinence pad is worn by said user;
a targeted pressure element established above at least a portion of said base; and
an absorbent established adjacent skin of said user when said incontinence pad is worn by said user.

148. An incontinence pad as described in clause 147, or any other clause, wherein said targeted pressure element is a raised ridge 149. An incontinence pad as described in clause 147, or any other clause, wherein said targeted pressure element is an upward, short length projection.

150. An incontinence pad as described in clause 147, or any other clause, wherein said targeted pressure element is configured to pressure the urethra of a male.

151. An incontinence pad as described in clause 150, or any other clause, wherein said targeted pressure element is a raised ridge.

152. An incontinence pad as described in clause 150, or any other clause, wherein pressure effected by said targeted pressure element acts transverse to a longitudinal axis of said urethra.

153. An incontinence pad as described in clause 147, or any other clause, wherein said targeted pressure element is configured to pressure the urethra of a female.

154. An incontinence pad as described in clause 153, or any other clause, wherein said targeted pressure element is an upward, short length projection.

155. An incontinence pad as described in clause 153, or any other clause, wherein pressure effected by said targeted pressure element acts substantially along a longitudinal axis of said urethra.

156. An incontinence pad as described in clause 153, or any other clause, wherein said targeted pressure element is configured for establishment directly below a urethral opening of a female wearing said pad.

157. A method to mitigate incontinence comprising the steps of:
establishing an absorbent pad in a genital area of a user;
creating a targeted pressure increase at a targeted location on said user through action of said absorbent pad; and
absorbing at least a substantial portion of any emissions from said user as a result of said incontinence within said absorbent pad.

158. A method as described in clause 157, or any other clause, wherein said step of creating a targeted pressure increase comprises the step of creating a targeted pressure increase through action of a raised ridge of said pad.

159. A method as described in clause 157, or any other clause, wherein said step of creating a targeted pressure increase comprises the step of creating a targeted pressure increase through action of a upward, short length projection of said pad.

160. A method as described in clause 157, or any other clause, wherein said step of creating a targeted pressure increase at a targeted location comprises the step of creating a targeted pressure increase at a perineum of a user.

161. A method as described in clause 160, or any other clause, wherein said step of creating a targeted pressure increase comprises the step of creating a targeted pressure increase to pressure on the urethra of a male.

162. A method as described in clause 160, or any other clause, wherein said step of creating a targeted pressure increase comprises the step of creating a targeted pressure increase through action of a raised ridge of said pad.

163. A method as described in clause 160, or any other clause, wherein said step of creating a targeted pressure increase comprises the step of creating a pressure that acts transverse to a longitudinal axis of said urethra.

164. A method as described in clause 157, or any other clause, wherein said step of creating a targeted pressure increase at a targeted location comprises the step of creating a targeted pressure increase at a urethral opening of a user.

165. A method as described in clause 164, or any other clause, wherein said step of creating a targeted pressure increase comprises the step of creating a targeted pressure increase to pressure the urethral opening of a female.

166. A method as described in clause 164, or any other clause, wherein said step of creating a targeted pressure increase comprises the step of creating a targeted pressure increase through action of an upward, short length projection of said pad.

167. A method as described in clause 164, or any other clause, wherein said step of creating a targeted pressure increase comprises the step of creating a pressure that acts substantially along a longitudinal axis of said urethra.

168. An incontinence pad comprising:
   a pad comprising an absorbent pad base, said pad having an outer surface capable of being established against clothing of a user when said pad is worn by said user;
   an inner surface of said pad, said inner surface opposite said outer surface;
   an urethral compressor attached to said pad along at least a portion of said inner surface; and
   an absorbent established adjacent skin of said user when said incontinence pad is worn by said user.

169. An incontinence pad as described in clause 168, or any other clause, wherein said urethral compressor is a raised ridge.

170. An incontinence pad as described in clause 168, or any other clause, wherein said urethral compressor is an upward, short length projection.

171. An incontinence pad as described in clause 170, or any other clause, wherein said upward, short length projection is substantially frusto-conical shaped.

172. An incontinence pad as described in clause 168, or any other clause, wherein said urethral compressor is configured to pressure the urethra of a male.

173. An incontinence pad as described in clause 172, or any other clause, wherein said urethral compressor is a raised ridge.

174. An incontinence pad as described in clause 172, or any other clause, wherein pressure effected by said urethral compressor acts transverse to a longitudinal axis of said urethra.

175. An incontinence pad as described in clause 168, or any other clause, wherein said urethral compressor is configured to pressure the urethra of a female.

176. An incontinence pad as described in clause 175, or any other clause, wherein said urethral compressor is an upward, short length projection.

177. An incontinence pad as described in clause 175, or any other clause, wherein pressure effected by said urethral compressor acts substantially along a longitudinal axis of said urethra.

178. An incontinence pad as described in clause 168, or any other clause, wherein said urethral compressor is configured for establishment directly below a urethral opening of a female wearing said pad.

179. A method to mitigate incontinence comprising the steps of:
   establishing an absorbent pad in a genital area of a user;
   creating urethral compression at a location on said user through action of said absorbent pad; and
   absorbing at least a substantial portion of any emissions from said user as a result of said incontinence within said absorbent pad.

180. A method as described in clause 179, or any other clause, wherein said step of creating urethral compression comprises the step of creating urethral compression through action of a raised ridge.

181. A method as described in clause 179, or any other clause, wherein said step of creating urethral compression comprises the step of creating urethral compression through action of a upward, short length projection.

182. A method as described in clause 179, or any other clause, wherein said step of establishing an absorbent pad in a genital area of a user comprises the step of establishing an absorbent pad in the genital area of a male user.

183. A method as described in clause 182, or any other clause, wherein said step of creating urethral compression at a location on said user through action of said absorbent pad comprises the step of creating urethral compression through action of a raised ridge.

184. A method as described in clause 182, or any other clause, wherein said step of creating urethral compression at a location on said user through action of said absorbent pad comprises the step of creating urethral compression through action of an upward, short length projection.

185. A method as described in clause 182, or any other clause, wherein said step of creating urethral compression comprises the step of creating urethral compression in a direction transverse to a longitudinal axis of said urethra.

186. A method as described in clause 182, or any other clause, wherein said step of creating urethral compression at a location comprises the step of creating urethral compression up against the urethra in the perineum area of said user.

187. A method as described in clause 179, or any other clause, wherein said step of establishing an absorbent pad in a genital area of a user comprises the step of establishing an absorbent pad in the genital area of a female user.

188. A method as described in clause 187, or any other clause, wherein said step of creating urethral compression at a location on said user through action of said absorbent pad comprises the step of creating urethral compression through action of an upward, short length projection.

189. A method as described in clause 188, or any other clause, wherein said upward, short length projection is configured for establishment substantially below a urethral opening of said user.

190. A method as described in clause 187, or any other clause, wherein said step of creating urethral compression comprises the step of creating urethral compression in a direction substantially along a longitudinal axis of said urethra.

191. An incontinence pad comprising:
   an absorbent pad base, said pad base having an outer surface capable of being established against clothing of a user when said pad is worn by said user;
   an inner surface of said pad, said inner surface opposite said outer surface;
   a nerve trigger element attached to and forming part of said pad along at least a portion of said inner surface; and
   an absorbent established adjacent skin of said user when said incontinence pad is worn by said user.

192. An incontinence pad as described in clause 191, or any other clause, wherein said nerve trigger element is a raised ridge.

193. An incontinence pad as described in clause 191, or any other clause, wherein said nerve trigger comprises an upward, short length projection.

194. An incontinence pad as described in clause 191, or any other clause, wherein said nerve trigger element affects a parasympathetic nerve.

195. An incontinence pad as described in clause 194, or any other clause, wherein said nerve trigger element compresses a nerve.

196. An incontinence pad as described in clause 195, or any other clause, wherein said nerve trigger element compresses said nerve during sitting by a user.

197. An incontinence pad as described in clause 195, or any other clause, wherein said nerve trigger element compresses said nerve via pressure caused by tight fitting briefs.
198. An incontinence pad as described in clause 191, or any other clause, wherein said nerve trigger element effects tightening of a urethral sphincter.
199. An incontinence pad as described in clause 191, or any other clause, wherein said nerve trigger element triggers a nerve upon compressing said nerve.
200. A method to mitigate incontinence comprising the steps of:
establishing an absorbent pad in a genital area of a user;
triggering at least one nerve reaction through action of said absorbent pad; and
absorbing at least a substantial portion of any emissions from said user as a result of said incontinence within said absorbent pad.
201. A method as described in clause 200, or any other clause, wherein said step of triggering comprises the step of triggering at least one nerve reaction through compressive action.
202. A method as described in clause 201, or any other clause, wherein said step of triggering at least one nerve reaction through compressive action comprises the step of triggering at least one nerve reaction through compressive action effected by a raised ridge.
203. A method as described in clause 201, or any other clause, wherein said step of triggering at least one nerve reaction through compressive action comprises the step of triggering at least one nerve reaction through compressive action effected by an upward, short length projection.
204. A method as described in clause 201, or any other clause, wherein said step of triggering comprises the step of triggering through compressive action effected by sitting.
205. A method as described in clause 201, or any other clause, wherein said step of triggering comprises the step of triggering through compressive action effected by tight fitting clothing worn over said absorbent pad.
206. A method as described in clause 200, or any other clause, wherein said step of triggering at least one nerve reaction comprises the step of triggering a parasympathetic nerve reaction.
207. A method as described in clause 200, or any other clause, wherein said step of triggering comprises the step of effecting tightening of a urethral sphincter.
208. An incontinence pad comprising:
an outer surface capable of being established against clothing of a user when said pad is worn by said user, said pad also defining a centerline;
an absorbent established adjacent skin of said user when said pad is worn by said user; and
a substantially longitudinal absorbency separator configured within at least a portion of said absorbent along said centerline.
209. An incontinence pad as described in clause 208, or any other clause, wherein said substantially longitudinal absorbency separator is established substantially in mid-sagittal plane of a wearer of said pad.
210. An incontinence pad as described in clause 208, or any other clause, wherein said substantially longitudinal absorbency separator is a liquid flow blocking wall.
211. An incontinence pad as described in clause 208, or any other clause, wherein said substantially longitudinal absorbency separator is established from a posterior end of said pad to an anterior end of said pad.
212. An incontinence pad as described in clause 208, or any other clause, wherein said substantially longitudinal absorbency separator is established to prevent flow of released liquid from a right side to a left side of said pad, and from a left side to a right side of said pad, when said pad is worn by a user.
213. An incontinence pad as described in clause 208, or any other clause, wherein said substantially longitudinal absorbency separator is structurally rigid.
214. An incontinence pad as described in clause 208, or any other clause, wherein said substantially longitudinal absorbency separator is compressible.
215. An incontinence pad as described in clause 208, or any other clause, wherein said substantially longitudinal absorbency separator is established as part of a raised ridge of said pad.
216. An incontinence pad as described in clause 208, or any other clause, wherein said pad comprises a raised ridge.
217. An incontinence pad as described in clause 216, or any other clause, wherein said substantially longitudinal absorbency separator is established within said raised ridge.
218. An incontinence pad as described in clause 216, or any other clause, wherein said substantially longitudinal absorbency separator is established below said raised ridge.
219. An incontinence pad as described in clause 208, or any other clause, wherein said pad comprises an upward, short length projection.
220. An incontinence pad as described in clause 219, or any other clause, wherein said substantially longitudinal absorbency separator is established below said upward, short length projection.
221. An incontinence pad as described in clause 208, or any other clause, wherein said substantially longitudinal absorbency separator is established within said absorbent.
222. An incontinence pad as described in clause 221, or any other clause, wherein said substantially longitudinal absorbency separator divides said absorbent into two sections.
223. A method to mitigate incontinence comprising the steps of:
establishing a pad having a centerline in a genital area of a user;
establishing an absorbent adjacent skin of said user;
absorbing at least a substantial portion of any emissions from said user as a result of said incontinence within said absorbent; and
substantially longitudinally separating absorption within said absorbent along at least a portion of said centerline.
224. A method as described in clause 223, or any other clause, wherein said step of substantially longitudinally separating absorption comprises the step of separating with a liquid flow blocking wall.
225. A method as described in clause 224, or any other clause, wherein said step of separating with a liquid flow blocking wall comprises the step of separating with a wall that is established from a posterior end of said pad to an anterior end of said pad.
226. A method as described in clause 224, or any other clause, wherein said wall is structurally rigid.
227. A method as described in clause 224, or any other clause, wherein said wall is compressible.
228. A method as described in clause 223, or any other clause, wherein said step of substantially longitudinally separating absorption comprises the step of preventing flow of released, absorbed liquid from a right side to a left side of said pad, and from a left side to a right side of said pad, when said pad is worn by a user.

229. A method as described in clause 223, or any other clause, wherein said step of substantially longitudinally separating absorption comprises the step of separating with a separator that forms part of a raised ridge.

230. A method as described in clause 223, or any other clause, wherein said step of substantially longitudinally separating absorption comprises the step of separating with a separator that passes below a raised ridge.

231. A method as described in clause 223, or any other clause, wherein said step of substantially longitudinally separating absorption comprises the step of separating with a separator that passes through an upward, short length projection, 232. A method as described in clause 223, or any other clause, wherein said step of substantially longitudinally separating absorption comprises the step of separating with a separator that passes below an upward, short length projection.

233. A method as described in clause 223, or any other clause, wherein said step of substantially longitudinally separating absorption comprises the step of separating with a separator that is established within said absorbent 234. An incontinence pad comprising:
an absorbent pad base, said absorbent pad base having an outer surface capable of being established against clothing of a user when said pad is worn by said user, said absorbent base having a centerline;
an inner surface of said pad, said inner surface opposite said outer surface; and
a substantially perpendicular structure attached to said pad and forming a portion of said inner surface along said centerline.

235. An incontinence pad as described in clause 234, or any other clause, wherein said perpendicular structure is a raised ridge 236. An incontinence pad as described in clause 234, or any other clause, wherein said perpendicular structure has substantially vertical sides when said pad is worn by a user.

237. An incontinence pad as described in clause 234, or any other clause, wherein said perpendicular structure has sides that are not substantially vertical but instead slope upwards from said pad on both right and left sides of said perpendicular structure.

238. A method to mitigate incontinence comprising the steps of:
establishing a pad having an absorbent pad base and an inner surface in a genital area of a user;
establishing a portion of said inner surface adjacent a perineum of said user; and
interposing a substantially perpendicular structure along at least a portion of said inner surface in the vicinity of at least a portion of said perineum of said user.

239. A method as described in clause 238, or any other clause, wherein said step of interposing a substantially perpendicular structure comprises the step of interposing a raised ridge.

240. A method as described in clause 238, or any other clause, wherein said step of interposing a substantially perpendicular structure comprises the step of interposing a perpendicular structure that has substantially vertical sides when said pad is worn by a user.

241. A method as described in clause 238, or any other clause, wherein said step of interposing a substantially perpendicular structure comprises the step of interposing a perpendicular structure that has sides that are not substantially vertical but instead slope upwards from said pad on both right and left sides of said perpendicular structure.

242. An incontinence pad comprising:
a primary fluid retention element having an outer surface capable of being established against clothing of a user when said incontinence pad is worn by said user, said primary retention element having a centerline;
a locationally separate secondary fluid retention element established adjacent said user on at least a portion of said centerline; and
an inner surface opposite said outer surface capable of being established adjacent skin of said user when said incontinence pad is worn by said user.

243. An incontinence pad as described in clause 242, or any other clause, wherein said locationally separate secondary fluid retention element is at least part of a raised ridge absorbant.

244. An incontinence pad as described in clause 242, or any other clause, wherein said locationally separate secondary fluid retention element is at least part of an upward, short length projection.

245. An incontinence pad as described in clause 242, or any other clause, wherein said locationally separate secondary fluid retention element defines a centerline that is established substantially along at least a portion of a longitudinal centerline defined by said pad.

246. An incontinence pad as described in clause 242, or any other clause, wherein said locationally separate secondary fluid retention element defines a centerline that is established within a sagittal plane of a wearer of said pad.

247. An incontinence pad as described in clause 242, or any other clause, wherein said locationally separate secondary fluid retention element is established between said base fluid retention element and skin of a wearer of said pad.

248. An incontinence pad as described in clause 242, or any other clause, wherein said primary fluid retention element is divided into substantially two halves by a substantially longitudinal absorbency separator.

249. An incontinence pad as described in clause 242, or any other clause, wherein said primary fluid retention element comprises a base fluid retention element.

250. An incontinence pad as described in clause 242, or any other clause, further comprising a fluidic communicator established to fluidically communicate said primary fluid retention element with said locationally separate secondary fluid retention element.

251. A method to mitigate incontinence comprising the steps of:
retaining fluid within a primary fluid retention element positioned substantially at a genital area of a user; and
locationally separately secondarily retaining fluid adjacent said user.

252. A method as described in clause 251, or any other clause, wherein said step of retaining fluid within a primary fluid retention element comprises the step of retaining fluid within a pad base absorbent or a raised ridge absorbent.

253. A method as described in clause 251, or any other clause, wherein said step of locationally separately secondarily retaining fluid adjacent said user comprises the step of retaining fluid within a raised ridge absorbent or a pad base absorbent.

254. A method as described in clause 251, or any other clause, wherein said step of locationally separately secondarily retaining fluid adjacent said user comprises the step of retaining fluid within a pad cup portion that is established towards the front of said pad.

255. A method as described in clause 251, or any other clause, further comprising the step of separating absorbed fluid into right and left fluid retention portions.

256. A method as described in clause 255, or any other clause, wherein said right and left fluid retention portions are of said pad base absorbent.

257. A method as described in clause 255, or any other clause, wherein said right and left fluid retention portions are of said raised ridge absorbent.

258. A method as described in clause 251, or any other clause, wherein said step of locationally separately secondarily retaining fluid adjacent said user comprises the step of locationally separately secondarily retaining fluid within a locationally separate secondary fluid retention element.

259. A method as described in clause 258, or any other clause, further comprising the step of fluidically communicating said primary fluid retention element with said locationally separate secondary fluid retention element.

260. An incontinence pad comprising:
  a pad base retention element having an outer surface capable of being established against clothing of a user when said incontinence pad is worn by said user, said pad base retention element having a centerline;
  a separate perineum retention element established above part of said primary retention element along at least a portion of said centerline; and
  an inner surface opposite said outer surface capable of being established adjacent skin of said user when said incontinence pad is worn by said user.

261. An incontinence pad as described in clause 260, or any other clause, wherein said separate perineum retention element comprises a urethral compressor.

262. An incontinence pad as described in clause 260, or any other clause, wherein said separate perineum retention element comprises a raised ridge.

263. An incontinence pad as described in clause 260, or any other clause, wherein said separate perineum retention element comprises a targeted pressure element.

264. A method to mitigate incontinence comprising the steps of:
  retaining fluid within a primary retention element positioned at a genital area of a user; and
  separately secondarily retaining at least a portion of said fluid.

265. A method as described in clause 264, or any other clause, further comprising the step of compressing a urethra of said user.

266. A method as described in clause 265, or any other clause, wherein said step of compressing a urethra of said user comprises the step of compressing said urethra with said primary retention element.

267. An incontinence pad comprising:
  an absorbent pad base, said pad having an outer surface capable of being established against clothing of a user when said pad is worn by said user and defining a centerline;
  an inner surface on a side of said pad that is opposite said outer surface; and
  a short length projection along at least a portion of said centerline and configured for positioning at a location below a urethra of said user user to mitigate at least some effects of incontinence.

268. An incontinence pad as described in clause 267, or any other clause, wherein said short length projection is substantially frusto-conical shaped.

269. An incontinence pad as described in clause 267, or any other clause, wherein said short length projection is an upward, short length projection.

270. An incontinence pad as described in clause 267, or any other clause, wherein said short length projection is configured for positioning at a location below a urethral opening of said user.

271. An incontinence pad as described in clause 270, or any other clause, wherein said user is female.

272. An incontinence pad as described in clause 267, or any other clause, wherein said short length projection is configured for positioning at a location below a urethra as it passes above a perineum of said user.

273. An incontinence pad as described in clause 272, or any other clause, wherein said user is male.

274. An incontinence pad as described in clause 267, or any other clause, wherein said short length projection is configured to apply pressure to said urethra.

275. An incontinence pad as described in clause 274, or any other clause, wherein said pressurization occurs during sitting by said user.

276. An incontinence pad as described in clause 274, or any other clause, wherein said pressurization is effected at least in part by briefs.

277. An incontinence pad as described in clause 276, or any other clause, wherein said briefs are tight fitting.

278. An incontinence pad as described in clause 274, or any other clause, wherein said pressurization is effected at least in part by the effect of a cord attached to said short length projection.

279. An incontinence pad as described in clause 267, or any other clause, wherein said short length projection is substantially frustoconical or conical in shape.

280. An incontinence pad as described in clause 267, or any other clause, wherein said short length projection is substantially cylindrical in shape.

281. An incontinence pad as described in clause 267, or any other clause, wherein said short length projection is substantially pyramidal in shape.

282. An incontinence pad as described in clause 267, or any other clause, wherein said short length projection is established atop a raised ridge.

283. An incontinence pad as described in clause 267, or any other clause, wherein said short length projection is repositionable on said absorbent pad base.

284. An incontinence pad as described in clause 283, or any other clause, wherein said short length projection is repositionable on said absorbent pad base with a hook and loop fastener.

285. An incontinence pad as described in clause 267, or any other clause, wherein said short length projection is an upward, short length projection.

286. A method to mitigate incontinence comprising the steps of:
  manufacturing a pad to have an absorbent pad base and an inner surface in a genital area of a user;
  manufacturing a short length projection so that it is adjacent a urethra of said user during wearing of said pad thereby; and
  absorbing at least a substantial portion of any emissions from said user as a result of said incontinence within said absorbent pad base.

287. A method as described in clause 286, or any other clause, wherein said step of manufacturing a short length projection comprises the step of establishing an upward, short length projection.
288. A method as described in clause 287, or any other clause, wherein said step of manufacturing a short length projection comprises the step of establishing a substantially frusto-conically shaped projection.
289. A method as described in clause 286, or any other clause, wherein said step of manufacturing a short length projection adjacent a urethra comprises the step of manufacturing said short length projection for positioning at a location below a urethral opening of said user.
290. A method as described in clause 289, or any other clause, wherein said user is female.
291. A method as described in clause 286, or any other clause, wherein said step of manufacturing a short length projection adjacent a urethra comprises the step of manufacturing said short length projection for positioning at a location below a urethra as it passes above a perineum of said user.
292. A method as described in clause 291, or any other clause, wherein said user is male.
293. A method as described in clause 286, or any other clause, wherein said step of manufacturing a short length projection comprises the step of step of manufacturing a short length projection to apply pressure to said urethra.
294. A method as described in clause 293, or any other clause, wherein said step of manufacturing a short length projection to apply pressure to said urethra comprises the step of manufacturing said short length projection to apply said pressure during sitting by said user.
295. A method as described in clause 293, or any other clause, wherein said step of manufacturing a short length projection to apply pressure to said urethra comprises the step of manufacturing said short length projection to apply said pressure that is effected at least in part by briefs.
296. A method as described in clause 295, or any other clause, wherein said briefs are tight fitting.
297. A method as described in clause 293, or any other clause, wherein said step of manufacturing a short length projection to apply pressure to said urethra comprises the step of manufacturing said short length projection to effect said pressure, or any other clause, wherein said pressure is effected at least in part through operation a cord attached to said short length projection.
298. A method as described in clause 286, or any other clause, wherein said step of manufacturing a short length projection comprises the step of manufacturing a short length projection that is substantially frustoconical in shape.
299. A method as described in clause 286, or any other clause, wherein said step of manufacturing a short length projection comprises the step of manufacturing a short length projection that is substantially cylindrical in shape.
300. A method as described in clause 286, or any other clause, wherein said step of manufacturing a short length projection comprises the step of manufacturing a short length projection that is substantially conical in shape.
301. A method as described in clause 286, or any other clause, wherein said step of manufacturing a short length projection comprises the step of manufacturing a short length projection that is substantially pyramidal in shape.
302. A method as described in clause 286, or any other clause, wherein said step of manufacturing a short length projection comprises the step of manufacturing a short length projection that is repositionable on said absorbent pad base.
303. A method as described in clause 302, or any other clause, wherein said step of manufacturing a short length projection that is repositionable on said absorbent pad base comprises the step of manufacturing a short length projection that is repositionable via hook and loop fastener.
304. An incontinence pad comprising:
  a compressible support area absorbent portion having an outer surface capable of being established against clothing of a user when said incontinence pad is worn by said user and an inner surface capable of being established against a skin surface of said user when said incontinence pad is worn by said user;
  an overflow absorbent portion established adjacent said compressible support area absorbent portion;
  a fluidic communicator fluidically connecting said compressible support area absorbent portion and said overflow absorbent portion; and
  a connection element connecting said compressible support area absorbent portion and said overflow absorbent portion.
305. An incontinence pad as described in clause 304, or any other clause, wherein said overflow absorbent portion comprises an intergluteal cleft area absorbent portion.
306. An incontinence pad as described in clause 304, or any other clause, wherein said overflow absorbent portion comprises a perineum area absorbent portion.
307. An incontinence pad as described in clause 304, or any other clause, wherein said fluidic communicator is fluid permeable.
308. An incontinence pad as described in clause 307, or any other clause, wherein said fluidic communicator comprises a material selected from the group consisting of: cotton, fibrous material, cloth, layered material, synthetic material and natural material.
309. An incontinence pad as described in clause 307, or any other clause, wherein said fluidic communicator is absorbent.
310. An incontinence pad as described in clause 304, or any other clause, wherein said compressible support area absorbent portion is compressed when a user of said pad sits on a surface.
311. An incontinence pad as described in clause 304, or any other clause, wherein said fluidic communicator is configured to allow passage of at least some fluid absorbed in said compressible support area absorbent portion from said compressible support area absorbent portion to said overflow absorbent portion.
312. An incontinence pad as described in clause 311, or any other clause, wherein fluid so passed is overflow of said compressible support area absorbent portion.
313. An incontinence pad as described in clause 311, or any other clause, wherein said fluidic communicator allows for two-way fluid passage.
314. An incontinence pad as described in clause 304, or any other clause, wherein said connection element comprises a connector selected from the group consisting of: integral connector, fibrous connector, thread connector, stitching connector and adhesive connector.
315. An incontinence pad as described in clause 304, or any other clause, wherein said connection element connects said compressible support area absorbent portion and said overflow absorbent portion at only a portion of said overflow absorbent portion.

316. An incontinence pad as described in clause 304, or any other clause, wherein said connection element connects said compressible support area absorbent portion and said overflow absorbent portion along an entire length of said overflow absorbent portion.
317. An incontinence pad as described in clause 304, or any other clause, wherein said overflow absorbent portion comprises a raised ridge.
318. An incontinence pad as described in clause 304, or any other clause, wherein said overflow absorbent portion comprises an upward projection.
319. An incontinence pad as described in clause 304, or any other clause, wherein said compressible support area absorbent portion and said overflow absorbent portion are both fluid retentive.
320. A method to mitigate fluid leakage from an incontinence pad, said pad defining an enclosed space between said pad and skin of a wearer of said pad, said method comprising the steps of:
    retaining fluid within a compressible support area absorbent portion positioned at a genital area of a user;
    establishing an overflow absorbent portion adjacent said compressible support area absorbent portion; and
    mitigating through action of said overflow absorbent portion, a tendency of said compressible support area absorbent portion to expel some of said retained fluid from said enclosed space upon compression of said compressible support area absorbent portion.
321. A method as described in clause 320, or any other clause, wherein said step of mitigating comprises the step of conveying said some of said retained fluid from said compressible support area absorbent portion to said overflow absorbent portion.
322. A method as described in clause 321, or any other clause, wherein said step of conveying occurs when external pressure is applied to said compressible support area absorbent portion.
323. A method as described in clause 322, or any other clause, wherein said external pressure is applied when said wearer of said pad sits down.
324. A method as described in clause 321, or any other clause, wherein said step of conveying comprises the step of conveying said some of said retained fluid during overflow from said compressible support area absorbent portion.
325. A method as described in clause 321, or any other clause, wherein said step of conveying comprises the step of conveying said some of said retained fluid through a fluidic communicator fluidically connecting said compressible support area absorbent portion and said overflow absorbent portion.
326. A method as described in clause 221, or any other clause, further comprising the step of retaining said expelled fluid in said overflow absorbent portion.
327. A method as described in clause 320, or any other clause, wherein said step of establishing an overflow absorbent portion comprises the step of establishing a intergluteal cleft area absorbent portion.
328. A method as described in clause 320, or any other clause, wherein said step of establishing an overflow absorbent portion comprises the step of establishing a perineum area absorbent portion.
329. A method as described in clause 320, or any other clause, wherein said step of establishing an overflow absorbent portion comprises the step of establishing a raised ridge absorbent portion.
330. A method as described in clause 320, or any other clause, wherein said step of establishing an overflow absorbent portion comprises the step of establishing a projection absorbent portion.
331. A pad as described in any of the preceding clauses, wherein an outer surface of said pad comprises a liquid impermeable outer surface.
332. A pad as described in any of the preceding clauses, wherein an inner surface of said pad comprises a one-way liquid impermeable inner surface.
333. A pad as described in any of the preceding clauses, wherein a base of said pad comprises a liquid absorbent material.
334. A pad as described in any of the preceding clauses, wherein said pad, when not in use and when placed such that its outer surface is on a lower supporting surface, when viewed from above, has a triangular shape, or any other clause, wherein said triangle defines a vertex and a base.
335. A pad as described in clause 334, or any other clause, wherein when said pad is worn by a user, said vertex of said triangular pad shape is towards a posterior side of said user, and said base of said triangular pad shape is towards an anterior side of said user.
336. A pad as described in any of the preceding clauses, wherein said pad, when not in use and when placed such that its outer surface is on a lower supporting surface, when viewed from the side, has a curved shape in at least one section thereof.
337. A pad as described in clause 336, or any other clause, wherein said pad, when not in use and when placed such that its outer surface is on a lower supporting surface, when viewed from the side, has a hammock shape.
338. A pad as described in any of the preceding clauses, wherein said pad, during use thereof by a user, extends from above the coccyx to above the pubic symphysis.
339. A pad as described in clause 338, or any other clause, wherein said pad extends from above the sacrum to above the pubic symphysis.
340. A pad as described in any of the preceding clauses, further comprising a raised ridge.
341. A pad as described in any of the preceding clauses, further comprising a cord forming part of and attached to said pad.
342. A pad as described in clause 341, or any other clause, wherein said cord comprises a manually graspable portion.
343. A pad as described in clause 341, or any other clause, further comprising a bias element.
344. A pad as described in any of the preceding clauses, further comprising a projection.
345. A pad as described in clause 344, or any other clause, wherein said projection is a raised ridge.
346. A pad as described in clause 344, or any other clause, wherein said projection, during wearing of said pad, is below a urethra.
347. A pad as described in clause 346, or any other clause, wherein said projection, during wearing of said pad, is below a urethral opening.
348. A pad as described in clause 347, or any other clause, wherein said projection is substantially frusto-conically shaped.
349. A pad as described in clause 347, or any other clause, wherein said projection is an upward, short length projection.

350. A pad as described in clause 346, or any other clause, wherein said projection is below a perineum of said user during wearing of said pad.
351. A pad as described in any of the preceding clauses, further comprising a targeted pressure element.
352. A pad as described in clause 351, or any other clause, wherein said targeted pressure element comprises a projection.
353. A pad as described in any of the preceding clauses, further comprising a urethral compression
354. A pad as described in clause 353, or any other clause, wherein said urethral compressor operates to apply a force that acts in a direction that is transverse to a longitudinal axis of the urethra.
355. A pad as described in clause 353, or any other clause, wherein said urethral compressor operates to apply a force that is parallel to a longitudinal axis of the urethra.
356. A pad as described in any of the preceding clauses, further comprising a nerve trigger element.
357. A pad as described in any of the preceding clauses, further comprising a substantially longitudinal absorbency separator.
358. A pad as described in any of the preceding clauses, further comprising a perpendicular structure.
359. A pad as described in any of the preceding clauses, further comprising a locationally separate secondary fluid retention element.
360. A pad as described in any of the preceding clauses, further comprising a primary retention element a separate perineum retention element.
361. A pad as described in any of the preceding clauses, further comprising a compressible support area absorbent portion, a bodily area absorbent portion established adjacent said compressible support area absorbent portion, and a connection element connecting said compressible support area absorbent portion and said bodily area absorbent portion.
362. A pad as described in clause 361, or any other clause, further comprising a fluidic communication element configured to fluidically connect said two portions.
363. A method as described in any of the preceding method clauses, further comprising the step of manually grasping a manually graspable cord portion of a cord attached to said pad.
364. A method as described in clause 363, or any other clause, further comprising step of applying localized pressure to the perineum of said user at least partially through use of said raised ridge of said pad is achieved, at least in part, through performance of the step of manually grasping a manually graspable cord attached to said pad.
365. A method as described in any of the preceding method clauses, further comprising step of establishing a raised ridge adjacent a perineum of a user.
366. A method as described in any of the preceding method clauses, further comprising the step of established a projection adjacent a perineum of a user.
367. A method as described in any of the preceding method clauses, further comprising step of establishing a projection adjacent a urethral opening of a user.
368. A method as described in any of the preceding method clauses, further comprising step of directionally biasing at least a portion of the pad with a cord that is attached to the pad at a cord attachment site.
369. A method as described in any of the preceding method clauses, further comprising step of creating urethral compression art a location on the user.
370. A method as described in any of the preceding method clauses, or any other clause, further comprising the step of triggering at least one nerve reaction through action of the pad.
371. A method as described in any of the preceding method clauses, or any other clause, further comprising the step of substantially longitudinally separating absorption within an absorbent.
372. A method as described in any of the preceding method clauses, or any other clause, further comprising the step of interposing a substantially perpendicular structure along at least a portion of the inner surface of the pad.
373. A method as described in clause 372, or any other clause, wherein said interposing a substantially perpendicular structure comprises the step of interposing a substantially perpendicular structure in the vicinity of a perineum of the pad wearer.
374. A method as described in clause 372, or any other clause, wherein said interposing a substantially perpendicular structure comprises the step of interposing a substantially perpendicular structure in the vicinity of a urethral opening of the pad wearer.
375. A method as described in any of the preceding method clauses, further comprising the step of locationally separately secondarily retaining fluid adjacent the user.
376. A method as described in any of the preceding method clauses, or any other clause, further comprising the step of separately secondarily retaining fluid within a perineum of the user.
377. A method as described in any of the preceding method clauses, further comprising the step of manufacturing a short length projection so that it is adjacent a urethra of the pad user during wearing of the pad thereby.
378. A method as described in any of the preceding method clauses, further comprising the step of mitigating, through action of an overflow absorbent portion, a tendency of the compressible support area absorbent portion to expel some of the retained fluid from the enclosed space between the pad and the user skin upon compression of the compressible support area absorbent portion.

What is claimed is:

1. An incontinence pad comprising:
a base having an outer surface capable of being established proximate clothing of a user when said incontinence pad is worn by said user, with said base having a centerline;
an absorbent filled, stiff urethral compressor established above at least part of said base on at least a portion of said centerline, said absorbent filled, stiff-urethral compressor having a left and a right side, wherein said left side is filled with absorbent material, wherein said right side is filled with absorbent material, and wherein said left side and said right side have roughly equalized fill amounts of absorbent material, and wherein said absorbent filled, stiff urethral compressor has a height, shape, and stiffness configured to effect application of a targeted, localized pressure against a urethra of said user, said targeted, localized pressure sufficient to substantially block urine flow through said urethra so as to mitigate incontinence;
an inner surface capable of being established adjacent tissue of said user when said incontinence pad is worn by said user; and
an anterior end and a posterior end of said absorbent filled, stiff urethral compressor, said absorbent filled, stiff urethral compressor configured so that, when said incontinence pad is worn by said user, said posterior end can be established and terminates adjacent an intergluteal cleft of said user while at least a portion of said urethral compressor is established proximate a perineum of said user, wherein said absorbent filled, stiff urethral compressor is also small enough, in width in a coronal plane cross-section, to provide said targeted, localized pressure against said urethra when said incontinence pad is worn by said user.

2. An incontinence pad as described in claim 1, wherein said urethral compressor has a shape selected from the group consisting of: substantially in the shape of a ridge, substantially in the shape of a pyramid, and substantially in the shape of the base of a pyramid.

3. An incontinence pad as described in claim 2, wherein said urethral compressor comprises a short length urethral compressor configured to apply pressure to a urethra of a female.

4. An incontinence pad as described in claim 3, wherein said urethral compressor is configured to pressurize said urethra from a side thereof.

5. An incontinence pad as described in claim 4, wherein said incontinence pad is configured to be established in a genital area of a female user.

\* \* \* \* \*